United States Patent
Scheidt et al.

(10) Patent No.: US 10,323,039 B2
(45) Date of Patent: Jun. 18, 2019

(54) ENANTIOSELECTIVE SYNTHESES OF HETEROYOHIMBINE NATURAL PRODUCT INTERMEDIATES

(71) Applicant: Northwestern University, Evanston, IL (US)

(72) Inventors: Karl A. Scheidt, Evanston, IL (US); Ashkaan Younai, Evanston, IL (US); Bi-Shun Zeng, Chicago, IL (US); Herbert Y. Meltzer, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/145,586

(22) Filed: May 3, 2016

(65) Prior Publication Data

US 2016/0326183 A1    Nov. 10, 2016

Related U.S. Application Data

(60) Provisional application No. 62/156,591, filed on May 4, 2015.

(51) Int. Cl.
| | | |
|---|---|---|
| *C07D 491/052* | (2006.01) | |
| *C07D 211/02* | (2006.01) | |
| *C07D 211/32* | (2006.01) | |
| *C07C 311/19* | (2006.01) | |

(52) U.S. Cl.
CPC ........ *C07D 491/052* (2013.01); *C07C 311/19* (2013.01); *C07D 211/02* (2013.01); *C07D 211/32* (2013.01)

(58) Field of Classification Search
CPC ................................................ C07D 491/052
See application file for complete search history.

(56) References Cited

U.S. PATENT DOCUMENTS

2006/0030608 A1    2/2006 Nelson et al.
2007/0254878 A1    11/2007 Cao et al.

FOREIGN PATENT DOCUMENTS

EP    0059817 A1    9/1982

OTHER PUBLICATIONS

Hirai, "Heterocycles in asymmetric synthesis. Part 2. Efficient asymmetric approaches to heteroyohimbine, yohimbine and related alkaloids." Journal of the Chemical Society, Perkin Transactions 1: Organic and Bio-Organic Chemistry 1992 (4), 517-24.*
Hirai, "Heterocycles in Asymmetric Synthesis. Part 1. Construction of the Chiral Building Blocks for Enantioselective Alkaloid Synthesis via an Asymmetric Intramolecular Michael Reaction" Journal of the Chemical Society, Perkin Transactions 1: Organic and Bio-Organic Chemistry 1992 (4), 509-516.*
van Tamelen "Total Syntheses of dl-Ajmalicine and Emetine." Journal of the American Chemical Society 1969, 91, 7359-7371.*
Otero and Nishikido "Esterifcation" 2nd ed. Wiley-VCH Weinheim 2010, p. 7.*
Greene and Wuts, Protective Groups in Organic Synthesis 3rd edition Wiley: New York, 1999 pp. 494-631.*
Korte, F. et al., "Newer Methods of Preparative Organic Chemistry II. 15. The Acyl-lactone Rearrangement, a Process for Preparing Heterocyclic Ring Systems", Angew. Chem. 1959, 71, 709-722.
Doyle, A. G. et al., "Small-molecule H-bond donors in asymmetric catalysis", Chem. Rev. 2007, 107, 5713-5743.
Auvil, T. J. et al., "Design Strategies for Enhanced Hydrogen-Bond Donor Catalysts", Eur. J. Org. Chem. 2014, 2014, 2633-2646.
Younai, A. et al., "Enantioselective Syntheses of Heteroyohimbine Natural Products: A Unified Approach through Cooperative Catalysis", Angewandte Chemie International edition, 2015, 54, No. 23, 6900-6904.
Palmisano, G. et al., "Heteroyohimbine alkaloids. Stereospecific conversion of ajmalicine into 19-epiajmalicine", J. Chem. Soc., Perkin Trans. 1, 1985, 923-926.
International Search Report and Written Opinion for PCT/US2016/030587 dated Oct. 27, 2016, 13 pages.

* cited by examiner

*Primary Examiner* — David K O'Dell
(74) *Attorney, Agent, or Firm* — Quarles & Brady LLP

(57) ABSTRACT

Enantioselective syntheses of cis- and trans-bicyclic dihydropyran compounds, and other intermediates, en route to heteroyohimbine alkaloids.

5 Claims, 6 Drawing Sheets

Figure 3

| entry | amine | additive | solvent | time (h) | % yield[a] | er[b] |
|---|---|---|---|---|---|---|
| 1 | A | - | THF | 36 | 99 | N/A |
| 2 | B | - | THF | 96 | 51 | 80:20 |
| 3 | C | - | THF | 120 | no rxn | - |
| 4 | D | - | THF | 120 | no rxn | - |
| 5 | E | - | THF | 120 | trace | - |
| 6 | E | TsOH | THF | 120 | no rxn | - |
| 7 | E | HCl | THF | 120 | no rxn | - |
| 8 | E | TFA | THF | 120 | no rxn | - |
| 9 | E | I | THF | 120 | 45 | 91:9 |
| 10 | F | I | THF | 120 | 45 | 96:4 |
| 11[c] | F | I | THF | 144 | 39 | 88:12 |
| 12[c] | F | II | THF | 96 | 43 | 93:7 |
| 13[c] | F[d] | II | THF | 120 | trace | - |
| 14[c] | F[d] | II | THF[e] | 120 | low conv[g] | - |
| 15[c] | F[d] | II | THF[f] | 120 | 51 | 91:9 |
| 16[c] | F[d] | II | THF[f] | 48 | 73 | 82:18 |
| 17[c] | F[d] | II | toluene[f] | 70 | 59 | 99:1 |
| 18[c] | F[d] | II | Et₂O[f] | 48 | 79 | 99:1 |
| 19[c] | F[d] | (R)-BINOL | CPME[f] | 120 | 65 | 99:1 |
| 20[c] | F[d] | III | CPME[f] | 120 | no rxn | - |

Rows grouped as: 1°-vs-2° amines (1–5); acids (6–8); H-bond donors (9–12); solvents and concentration (13–20).

ENANTIOSELECTIVE SYNTHESES OF HETEROYOHIMBINE NATURAL PRODUCT INTERMEDIATES

This application claims priority to and the benefit of application Ser. No. 62/156,591 filed on May 4, 2015, the entirety of which is incorporated herein by reference.

BACKGROUND OF THE INVENTION

Alstonine (1) and serpentine (2) are pentacyclic alkaloids proposed to contain a zwitterionic indolo[2,3-a]quino-liz-idine, referred to as an anhydronium base (FIG. 1A). This structural motif is rare among natural products and is especially unusual in total synthesis, with the only examples being strychnoxanthine (3) and melinonine-E (4). Alstonine has recently been identified as the major component of a plant-based treatment used in Nigeria by traditional healers to treat psychotic disorders. However, the scarcity and lack of purity from natural sources, as well as the uncertainty regarding its exact mechanism of action, illustrates the need for an asymmetric synthesis to enable further study. The related trans diastereomer, serpentine, exhibits anticancer and antimalarial properties and there have been limited efforts at elucidating its mechanism of action.

The closely related heteroyohimbine family of alkaloids (FIG. 1B) has elicited the interest of numerous synthetic groups for multiple decades, with representative alkaloids of this family including tetrahydroalstonine (5), akuammigine (6), and ajmalicine (7). These natural products are structurally similar to alstonine and serpentine, only differing in ring saturation and relative stereochemistry at C3 and C20 (FIG. 1B). Though 80 years have passed since the first isolations of alstonine (from *Alstonia constricta*) and serpentine (from *Rauvolfia serpentina*), surprisingly, no total syntheses of these specific compounds have been reported to date. Accordingly, there remains an on-going search in the art for enantioselective syntheses of these and other such indole alkaloids and their natural product progenitors (e.g., 5 and 6).

SUMMARY OF THE INVENTION

In light of the foregoing, it is an object of the present invention to provide enantioselective syntheses and related natural products and intermediates thereof, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to design a synthetic pathway to structurally-related heteroyohimbine natural products, each through a common enantioenriched intermediate.

It can be another object of the present invention to provide a cooperative hydrogen bonding/enamine-catalyzed Michael addition reaction, to provide such an enantioenriched intermediate compound.

It can be another object of the present invention, alone or in conjunction with one or more of the preceding objectives, to provide enantioselective syntheses of several heteroyohimbine natural products, including the first total synthesis of alstonine and serpentine, at yields enabling sufficient quantities for further study and development of antipsychotic drugs.

Other objects, features, benefits and advantages of the present invention will be apparent from this summary and the following descriptions of certain embodiments, and will be readily apparent to those skilled in the art knowledgeable in the design of enantioselctive reaction pathways and related synthetic techniques. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a method for asymmetric intramolecular Michael addition. Such a method can comprise providing a keto-enamine ester of a formula

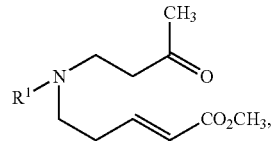

wherein $R^1$ can be selected from H and amino protecting groups; and intramolecular cyclization of such an ester with a chiral amine compound, in the presence of an H-bond donor, to provide a trans-piperdinyl compound of a formula

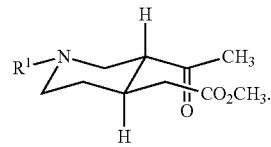

In certain non-limiting embodiments, such an amine compound can be selected from pyrrolidine and (R)-1-(naphthalene-1-yl)ethanamine. In certain such embodiments, such an H-bond donor compound can be catechol. Regardless, cyclization can be undertaken in a cyclopentyl methyl ether solvent. As a separate consideration, as illustrated below, $R^1$ can be a tosylate (Ts) protecting group.

Accordingly, with provision of such a piperdinyl compound, this invention can also be directed to a method of preparing a trans-bicyclic dihydropyran compound. Such a method can comprise providing a trans-piperdinyl compound of a formula

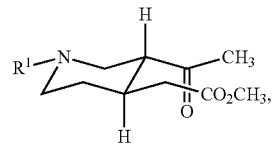

wherein $R^1$ can be selected from H and amino protecting groups; reduction of the ketone moiety of such a piperdinyl compound to provide a hydroxy ester compound of a formula

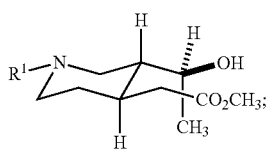

condensation of the hydroxy and ester moieties of such a hydroxy ester compound to provide a lactone compound of a formula

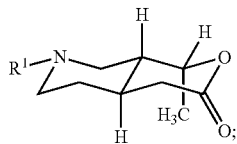

acylation of such a lactone compound, in the presence of an acid catalyst to promote reductive elimination of the carbonyl moiety of such a lactone and provide a trans-bicyclic dihydropyran compound of a formula

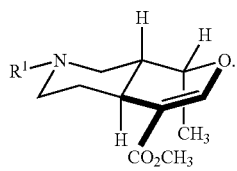

In certain embodiments, condensation can be promoted with p-toluenesulfonic acid. Regardless, without limitation, acylation can be achieved with methyl formate and acyl chloride. In certain such embodiments, polyphosphoric acid can be a useful acid catalyst. As a separate consideration, $R^1$ can be a tosylate (Ts) protecting group.

Alternatively, with provision of such a hydroxy ester compound of the sort described above, the present invention can also be directed to a method of preparing a cis-bicyclic dihydropyran compound. Such a method can comprise providing a hydroxy ester compound of a formula

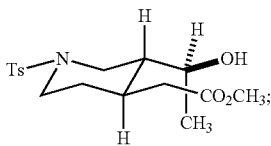

dehydration of such a hydroxy ester and reprotection of the amine moiety of such a compound with a carbamate protecting group to provide an alkene compound of a formula

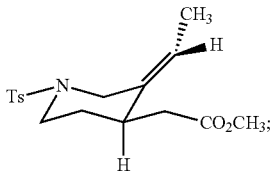

and hydroboration of such an alkene compound to promote formation of a lactone compound of a formula

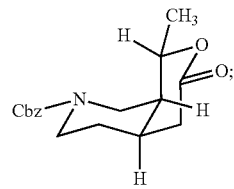 [SMILES: CC1OC(=O)CC2CCN(C(=O)OCc3ccccc3)CC21]

and acylation of such a lactone compound, in the presence of an acid catalyst to promote reductive elimination of the carbonyl moiety of such a lactone and provide a cis-bicyclic dihydropyran compound of a formula

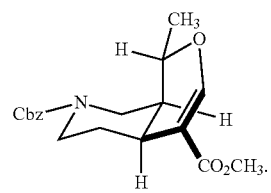

In certain embodiments, dehydration can be achieved with sodium iodide. In certain such embodiments, without limitation, reprotection can be achieved with magnesium metal and benzyl carbamate. Regardless, hydroboration can be achieved with 9-borabicyclo[3.3.1]nonane. In certain embodiments, acylation can be achieved with sodium hydride and acyl chloride, with an acid catalyst such as can be but is not limited to p-toluenesulfonic acid. As a separate consideration, such a benzyl carbamate protecting group can be removed via hydrogenation over palladium-carbon.

In part, as can be used in conjunction with or result from the present methodologies, this invention can also be directed to one or more compounds prepared as summarized above and described more fully below. Such compounds include but are not limited to

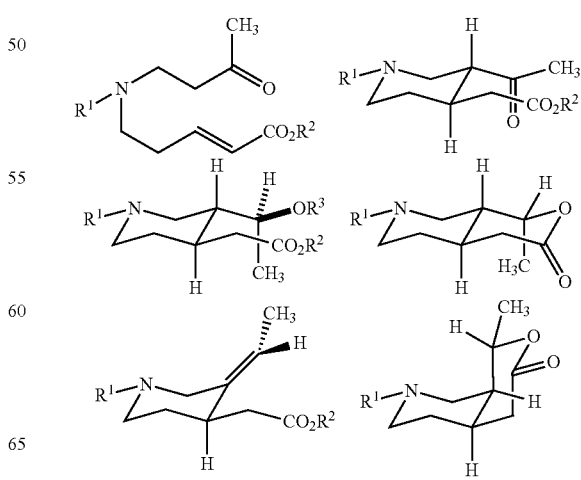

-continued

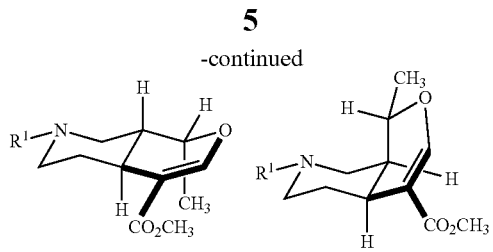

wherein $R^1$ can be selected from H and amino protecting groups; $R^2$ can be selected from $C_1$-about $C_6$ alkyl moieties; and $R^3$ can be selected from H and hydroxy protecting groups. In certain non-limiting embodiments, $R^1$ can be selected from tosylate (Ts) and benzyl carbamate (Cbz) protecting groups; and, independently, $R^2$ can be methyl.

BRIEF DESCRIPTION OF THE DRAWINGS

FIGS. 2-6. (2) Retrosynthetic for alstonine and serpentine via 15. (3) Optimization of Enamine Catalyzed Michael Addition. [a]Isolated yield. [b]Determined by HPLC analysis. Reaction conducted at 40° C. [d]30 mol % amine used. [e]Reaction carried out at 0.5 M. [f]Reaction carried out at 1.0 M. [g]<50% consumption of 16 observed by NMR spectroscopy after 120 h, product not isolated. (4) Preparation of Bicyclic Lactones Conditions: (a) $NaBH_4$, $CH_3OH/THF$, −20° C., 97%; (b) TsOH, benzene, 80° C., 68%; (c) MsCl, pyridine, 89%; (d) NaI, acetone, 60° C., (e) DBU, benzene, 80° C., 78% (over 2 steps); (f) $Mg°$, $CH_3OH$, then CbzCl, $K_2CO_3$, EtOAc, 70%; (g) 9-BBN, THF, 60° C., then $CH_3OH$, NaOH. $H_2O_2$, 0° C., (h) TsOH, benzene, 51% (over 2 steps). (5)-(6) Schematic x-ray structures for compounds 15 and 19, respectively.

DETAILED DESCRIPTION OF CERTAIN EMBODIMENTS

Figure 1A:
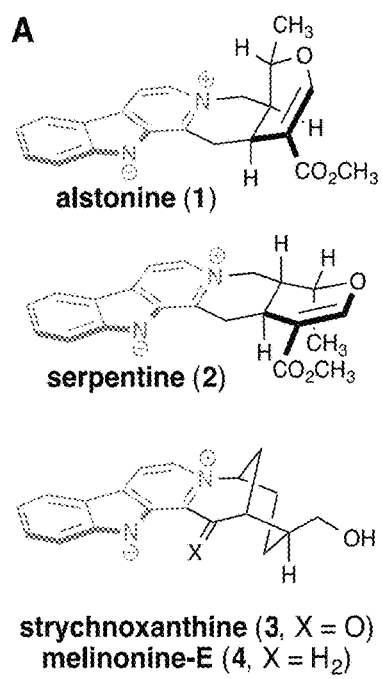
FIGS. 1A-B. (A) Examples of known anhydronium base natural products; (B) Structurally related heteroyohimbine alkaloids.
Figure 1B:
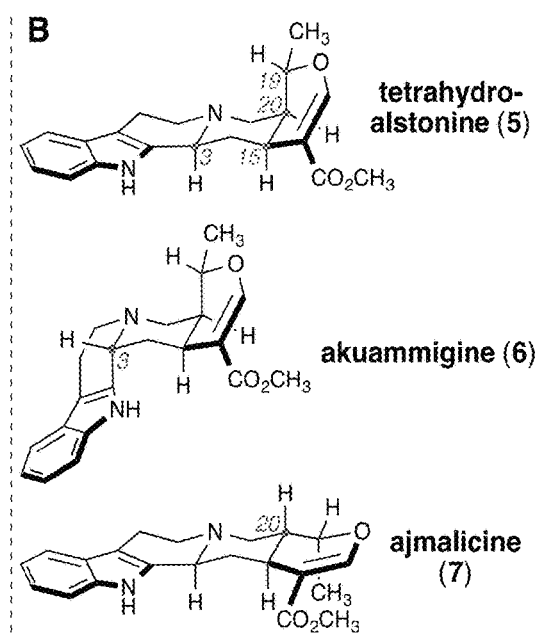
Figure 2:
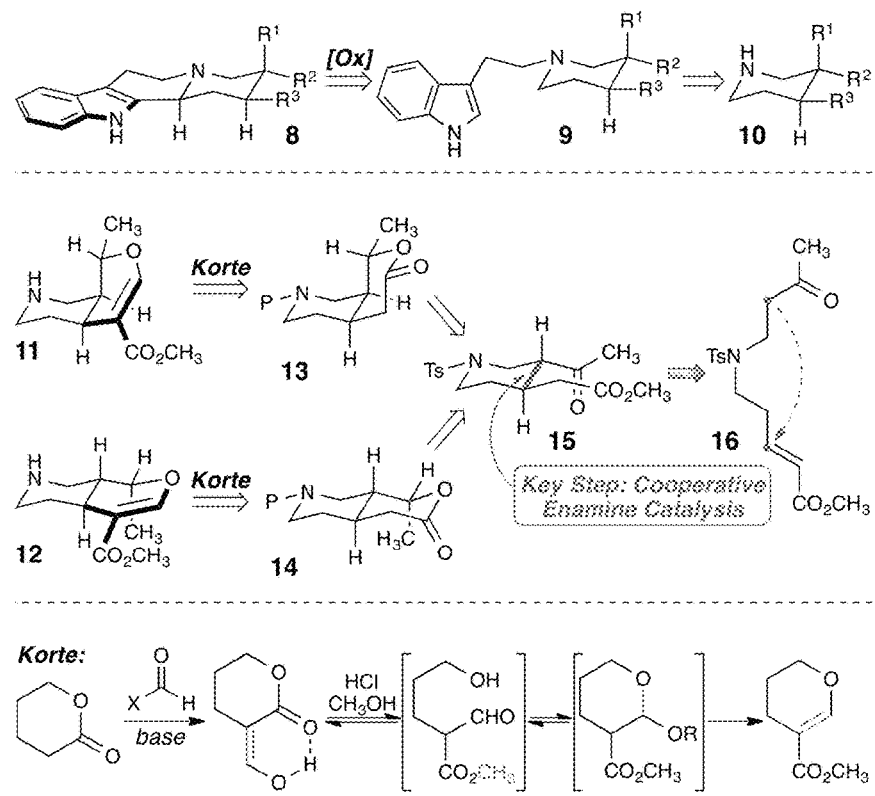

Illustrating certain non-limiting embodiments of this invention, a synthetic approach towards alstonine and serpentine focused on the corresponding heteroyohimbine alkaloids tetrahydroalstonine (5) and ajmalicine (7) respectively. Both of these intermediates can be derived in principle from the corresponding bicyclic dihydropyrans through successive N-functionalization (reductive amination and oxidative iminium ion cyclization (8→9→10, FIG. 2). These dihydropyran stereoisomers (11 and 12) can be obtained through a known "acyl-lactone rearrangement" from the corresponding lactones (13 and 14), a reaction first disclosed by Korte. (Korte, F.; Büchel, K. H. Angew. Chem. 1959, 71, 709-722.) Both diastereomers of the bicyclic lactone can be derived from the same trans-substituted piperidine (15), which was initially thought could be assembled through what at first seemed to be a straightforward enamine-catalyzed intra-molecular Michael reaction. Asymmetric enamine catalysis is a field that has seen tremendous innovation in the past 15 years. (The large majority of publications utilizing enamine catalyzed Michael additions have involved the use of electron deficient Michael acceptors such as alkylidene malonates, nitro-olefins, and vinyl ketones. For more challenging transformations, additives such as Brønsted acids, H-bond donors, and Lewis acids, which generally facilitate conversion by activation of the electrophile, are employed.) Given all of this innovation, it is surprising and unexpected that asymmetric intra-molecular Michael additions into simple unsaturated esters still remains underexplored, with reported examples typically involving stoichiometric amine and extended reaction times (3-4 weeks). As an approach toward the aforementioned trans-piperidine, stoichiometric pyrrolidine (FIG. 3, entry 1) was used in reaction with linear precursor 16 (obtained in 41% yield over four steps from 3-amino-1-propanol; see examples) to obtain (±)-15.

Known chiral secondary amines (FIG. 3, entries 2-4) were evaluated, but these sterically congested amines surprisingly did not afford any desired product in a reasonable time (<120 h). Trace amounts of product were observed after 120 h when using stoichiometric α-methylbenzylamine (E, entry 5), but again, much more rapid conversion with high levels of selectivity was desired. To this end, it was thought to utilize an additive to activate the unreactive enoate electrophile and drive conversion.

In an initial additive screen, Brønsted acids (entries 6-8) had no effect on conversion, however the addition of a stoichiometric amount of Schriener's thiourea (I, entry 9) promoted the full consumption of 16 within a desired timeframe. Unfortunately, this reaction was plagued by the formation of several undesired side-products, though the product could be isolated in modest yield and good enantioselectivity. This result suggested involvement of an H-bond donor to activate the previously unreactive ester. (For reviews of asymmetric H-bond donor catalysis, see: (a) Doyle, A. G.; Jacobsen, E. N. Chem. Rev. 2007, 107, 5713-5743; (b) Auvil, T. J.; Schafer, A. G.; Mattson, A. E. Eur. J. Org. Chem. 2014, 2014, 2633-2646.) By switching to the more sterically demanding primary amine F (entry 10), the enantioselectivity could be increased. Then, switching the H-bond donor to catechol (II, entry 12) and increasing the temperature to 40° C., complete consumption of 16 was observed in only 96 h, but yield and selectivity were diminished slightly. Catalysis was desired with the amine and it was found that increasing the concentration facilitated this goal (entries 13-15). Finally, changing the solvent had drastic effects on conversion and selectivity, with cyclopentyl methyl ether (CPME) being the optimal solvent (entry 18), providing 15 in good yield and excellent enantioselectivity in just 48 h. Gratifyingly, the optimized catalysis conditions could be scaled up to provide multi-gram quantities of enantioenriched piperidine 15 (absolute stereochemistry determined by X-ray crystallographic analysis, but not shown). Finally, because catechol is an unconventional H-bond donor, its role in activating the substrate was assessed. To this end, catechol was substituted with a mono-phenol (III) with a nearly identical pKa (entry 20), but observed no reaction after 120 h, supporting the notion that catechol has a role beyond that of a simple Brønsted acid.

Figure 4:
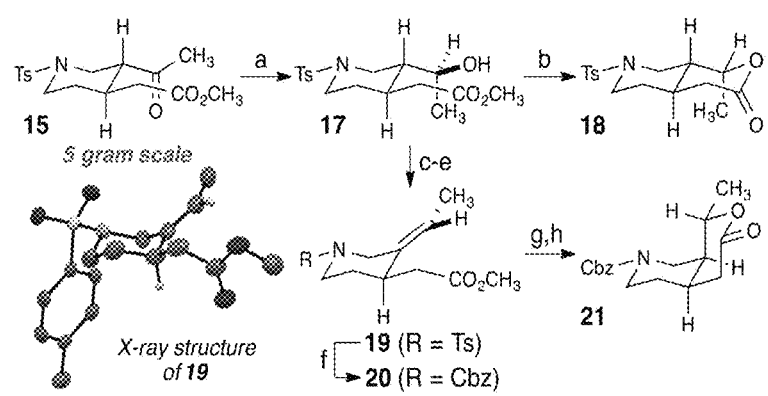

With enantioenriched 15 in hand, the next phase was to elaborate this structure to the desired bicyclic lactones for both alstonine and serpentine. First, ketone reduction of 15 provided alcohol 17 in excellent yield as a single diastereomer (FIG. 4). The trans-lactone (18) required for serpentine was obtained in acceptable yield (68%) by lactonization of 17 with TsOH. To craft the cis-lactone for the synthesis of alstonine, alcohol 17 was carried through a three-step inversion and elimination sequence to obtain Z-alkene 19 in very good yield (olefin geometry confirmed by X-ray crystallographic analysis, but not shown). With this particular olefin geometry, si-face hydroboration/oxidation would provide the proper relative stereochemistry for the alstonine scaffold. However, this substrate was found to be unreactive to various borane sources even under forcing conditions, possibly due to the electron withdrawing allylic sulfonamide limiting the capacity for electrophilic substitution by boron. By removing the tosylate and re-protecting with the less electron-withdrawing benzyl carbamate (Cbz), it was possible to obtain cis-lactone 21 through the desired hydroboration-oxidation and lactonization sequence in moderate yield. (Interestingly, when attempting to use a N-Cbz derivative of 16 in the present cooperative catalysis reaction (not shown), this substrate was found to be substantially less reactive. It is surmised that the higher Lewis basicity of the carbamate relative to the sulfonamide or methyl ester limits the desired H-bond activation.)

The acylation of lactones 18 and 21 with methyl formate provided the requisite α-formyl lactones (not shown) for the Korte rearrangement (Scheme 2). In the case of the acyl lactone derived from 18, exposure to methanolic HCl did not provide the desired dihydropyran. Instead, acetal 22a was observed as the major product, which is the intermediate directly preceding the elimination in the reported mechanism of this rearrangement. Although prolonged exposure to methanolic HCl did not facilitate the desired elimination, the use of catalytic polyphoshoric acid with this intermediate acetal provided dihydropyran 23 in good yield (67%) over the 3-step sequence from 18. In the case of cis-lactone 21, the acetal corresponding to the interrupted Korte rearrangement (22b) was not observed, with the expected dihydropran 25 being isolated as the major product in good (56%) yield after exposure to methanolic HCl. A possible cause for this difference in reactivity may be the conformation of the C19 methyl group, which is axial in trans-fused system as opposed to equatorial in the cis-fused system. The axial methyl group in acetal 22a could hinder the necessary anti-periplanar elimination of the methoxy substituent through 1,3-diaxial strain, which would be absent in the corresponding cis-fused system 22b. Subsequent deprotection of purified bicyclic dihydropyrans 23 and 25 followed by reductive amination with indole-3-acetaldehyde provided 2,3-secoajmalicine (24) and 2,3-secoakuammigine (26) respectively.

With the aforementioned intermediates in hand, and as relates to certain non-limiting embodiments, utility of this invention can be demonstrated by final synthesis of the desired natural products. At this juncture, a biomimetic cyclization approach was evaluated since the biosynthetic pathways for many indole alkaloids are presumed to involve monoamine oxidase triggered C—C bond cyclizations. While the N-oxides of 25 and 26 could be accessed via smooth oxidation with DMDO (not shown) the exposure of either compound to a host of acylation species and conditions unfortunately provided very low yields of the desired products (i.e., 5 and 7). The combination of indole-3-acetaldehyde and a free amine (i.e., 11 and 12) was also considered, to promote a compelling redox neutral iminium ion formation, isomerization and Pictet-Spengler based on inspiring reports by Seidel (not shown). However, these systems were shown to be unproductive under numerous conditions surveying solvent, acid additives and dehydrating agents. Ultimately, the desired oxidative iminium ion cyclization was accomplished based on precedent involving mercuric acetate/EDTA to afford the natural products ajmalicine (7) and tetrahydroalstonine (5) in modest yield, consistent with previous reports.

Scheme 1$^a$

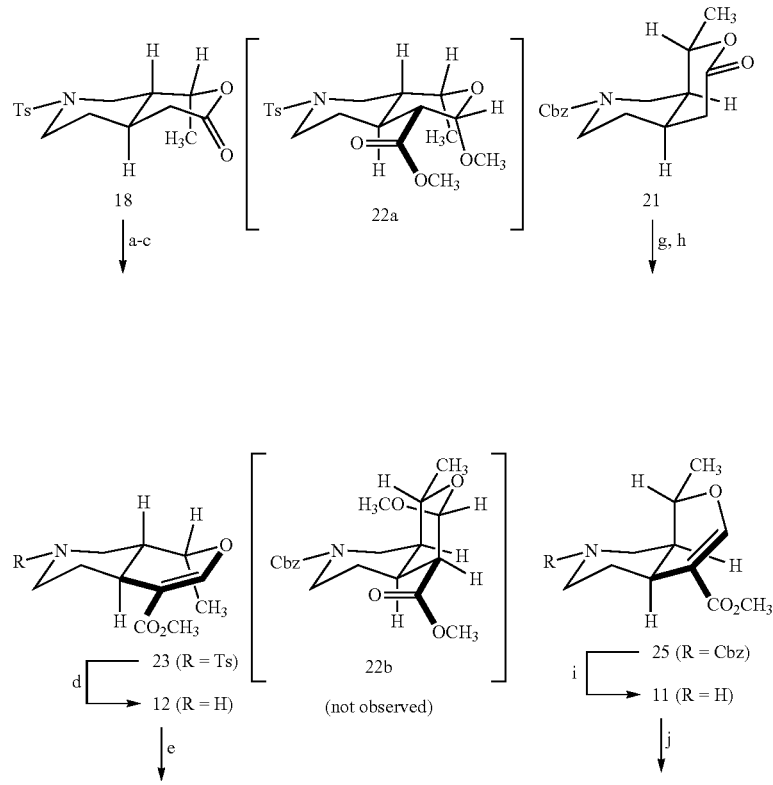

-continued

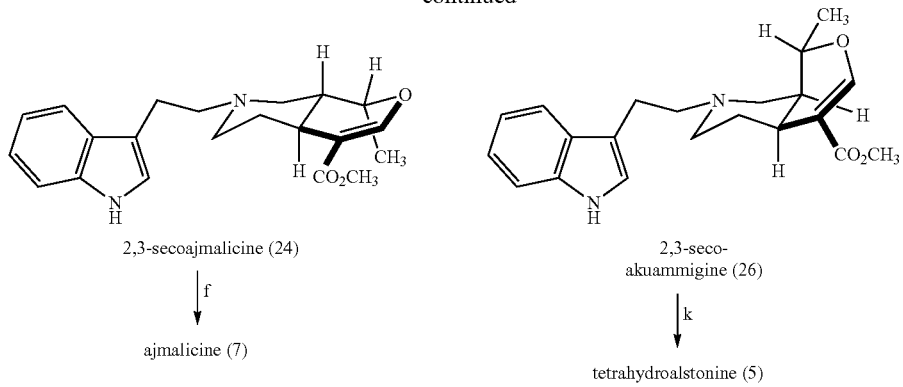

2,3-secoajmalicine (24)   2,3-seco-akuammigine (26)

↓ f                        ↓ k ajmalicine (7)             tetrahydroalstonine (5)

<sup>a</sup>Conditions: (a) tBuOK, methyl formate, THF; (b) AcCl, CH$_3$OH, 60° C.; (c) polyphosphoric acid, benzene, 80° C., 67% (over 3 steps); (d) Mg°, CH$_3$OH, 75%; (e) indole-3-acetaldehyde, NaBH(OAc)$_3$, CH$_2$Cl$_2$, 67%; (f) Hg(OAc)$_2$, EDTA disodium salt, AcOH/H$_2$O, 80 to 100° C., then NaBH$_4$, CH$_3$OH, 0° C., 45%; (g) NaH, methyl formate, THF; (h) AcCl, CH$_3$OH, 60° C., 56% (over 2 steps); (i) 10% Pd/C, H$_2$ (balloon), EtOH, 99%, (j) indole-3-acetaldehyde, NaBH(OAc)$_3$, CH$_2$Cl$_2$, 66%. (k) Hg(OAc)$_2$, EDTA disodium salt, AcOH/H$_2$O, 80° C., then NaBH$_4$, CH$_3$OH, 0° C., 41%.

As the last transformations, the aromatization of the β-carboline subunits of ajmalicine and tetrahydroalstonine was necessary to produce the requisite, final anhydronium base functionality. This final transformation was accomplished through a palladium black mediated dehydrogenation to obtain the corresponding β-carbolinium salts (Scheme 2).

Scheme 2<sup>a</sup>

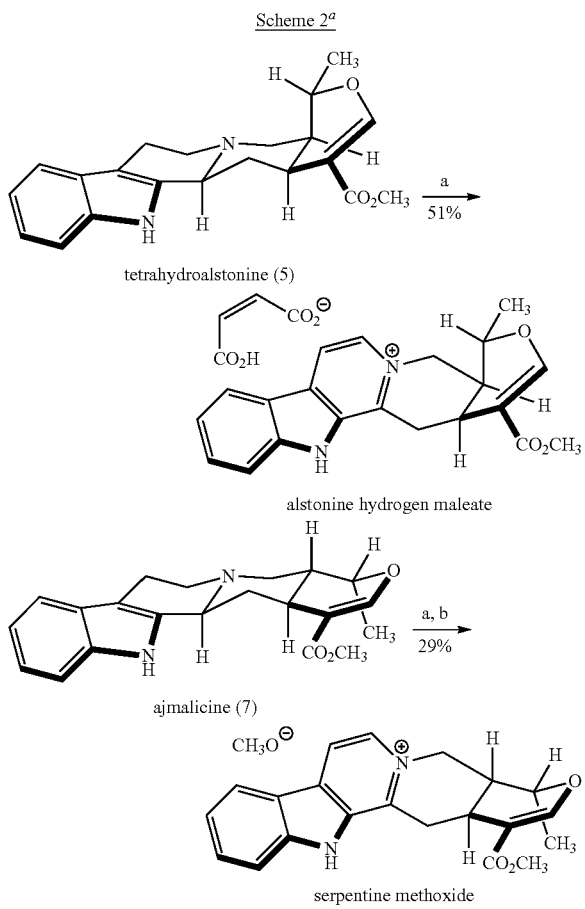

tetrahydroalstonine (5)

↓ a, 51% alstonine hydrogen maleate ajmalicine (7)

↓ a, b, 29% serpentine methoxide

<sup>a</sup>Conditions: (a) Pd black, maleic acid, H$_2$O, 100° C.; (b) NaOH, CH$_3$OH/H$_2$O.

As for the reported zwitterionic functionality of 1 and 2, pH dependent UV-vis and NMR spectroscopic studies of other anhydronium base natural products have shown the indole nitrogen is only deprotonated at elevated pH (>10). Of note for alstonine, the initial isolation paper noted high instability for the neat free base form of the natural product. Decomposition of the β-carbolinium salts was observed upon exposure to dilute aqueous NaOH, however an analytical sample of serpentine was recovered. Interestingly, $^1$H and $^{13}$C NMR signals for this recovered sample matched both the pre-basified mixture as well as an authentic sample of a commercial sample of serpentine hydrogen tartrate salt. This is in line with reports that these compounds exist as salts in protic solvents. Data for the hydrogen maleate salt form of alstonine matches the authentic sample as well. While ambiguity exists in the literature regarding exact counter-ion associated with the natural products at isolations and testing, the reported UV-vis and NMR data suggests the natural products predominately have the indole N—H present (vs. the zwitterionic form commonly drawn). Importantly, the successful routes outlined herein are fueling further needed investigations on this topic.

In conclusion, the first total syntheses of alstonine and serpentine were accomplished through use of the present invention, in particular with a novel cooperative H-bond donor/enamine catalysis reaction as a common synthetic step toward several intermediates. These scalable routes highlight the need for continued catalysis research in the context of total synthesis and lay the foundation for further study of the biological activity of these unique alkaloids, particularly in the realm of neurotherapeutics.

Examples of the Invention

The following non-limiting examples and data illustrate various aspects and features relating to the methods and compounds of the present invention, including the preparation of various heteroyohimbine intermediate compounds, as are available through the synthetic methodologies described herein. In comparison with the prior art, the present methods provide results and data which are surprising, unexpected and contrary thereto. While the utility of this invention is illustrated through the preparation of several intermediate compounds, moieties and substituents thereof, it will be understood by those skilled in the art that comparable results are obtainable through the preparation of several other intermediate compounds and corresponding moieties and substituents, as are commensurate with the scope of this invention.

General Information

All reactions were carried out under a nitrogen atmosphere in oven-dried glassware with magnetic stirring. All organic solvents were purified by passage through a bed of activated alumina. Reagents were purified prior to use unless otherwise stated following the guidelines of Chai and Armarego, as provided in the literature. Purification of reaction products was carried out by flash chromatography using EM Reagent or Silicycle silica gel 60 (230-400 mesh). Analytical thin layer chromatography was performed on EM Reagent 0.25 mm silica gel 60-F plates. Visualization was accomplished with UV light and ceric ammonium nitrate stain, potassium permanganate stain or ninhydrin stain followed by heating. Infrared spectra were recorded on a Bruker Tensor 37 FT-IR spectrometer. $^1$H NMR spectra were recorded on a Bruker Avance 500 MHz w/direct cryoprobe (500 MHz) spectrometer and are reported in ppm using solvent as an internal standard (CDCl$_3$ at 7.26 ppm). Data are reported as (ap=apparent, s=singlet, d=doublet, t=triplet, q=quartet, m=multiplet, br=broad; coupling constant(s) in Hz, integration). Proton-decoupled $^{13}$C NMR spectra were recorded on a Bruker Avance 500 MHz w/direct cryoprobe (125 MHz) spectrometer and are reported in ppm using solvent as an internal standard (CDCl$_3$ at 77.16 ppm). Mass spectra data were obtained on a Waters Acquity-H UPLC-MS with a single quadrupole ESI Spectrometer or on a Gas Chromatography Mass Spectrometer (Agilent 7890A/5975C GCMS System).

Example 1

N-(3-Hydroxypropyl)-4-methylbenzenesulfonamide (I)

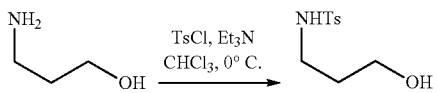

To a cooled (0° C.) mixture of 3-aminopropan-1-ol (1.9 mL, 24.8 mmol) and Et$_3$N (6.9 mL, 49.6 mmol, 2.0 equiv) in chloroform (4.0 mL) was added a solution of p-toluenesulfonyl chloride (5.21 g, 14.38 mmol, 1.1 equiv) in chloroform (6.0 mL, 2.5 M overall). The mixture was allowed to slowly warm to ambient temperature and stir under inert atmosphere for 18 h. The reaction was then quenched with 5% NaHCO$_3$, and the mixture was extracted with EtOAc (×3). The combined organic layers were washed successively with 5% citric acid, water, 5% NaHCO$_3$, and brine. Then the organic layers were dried over MgSO$_4$, filtered, and concentrated in vacuo to provide N-(3-hydroxypropyl)-4-methylbenzenesulfonamide (5.70 g, 24.8 mmol, 99% yield). Carried on to next step without further purification.

Analytical data for I: $^1$H NMR (400 MHz, CDCl$_3$) δ 7.76 (d, J=8.3 Hz, 2H), 7.35-7.29 (m, 2H), 5.62 (t, J=6.1 Hz, 1H), 3.70 (t, J=5.8 Hz, 2H), 3.07 (q, J=6.3 Hz, 2H), 2.74 (s, 1H), 2.43 (s, 3H), 1.71 (ap p, J=6.0 Hz, 2H). $^1$H NMR data for this product corresponds with literature values.

Example 2

4-Methyl-N-(3-oxopropyl)benzenesulfonamide (II)

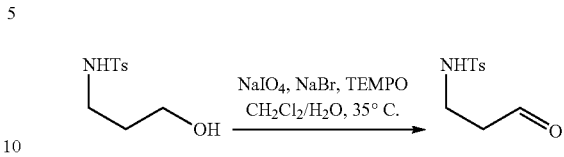

To a mixture of N-(3-hydroxypropyl)-4-methylbenzenesulfonamide (1.15 g, 5.00 mmol), TEMPO (0.078 g, 0.50 mmol, 0.10 equiv), NaIO$_4$ (1.77 g, 8.25 mmol, 1.65 equiv) and NaBr (0.085 g, 0.825 mmol, 0.165 equiv) was added CH$_2$Cl$_2$/H$_2$O (45:55, 20.0 mL, 0.25 M). The resulting biphasic mixture was heated to 35° C. Upon completion of the reaction (18 h; monitored by TLC), the organic layer was separated, and the aqueous layer was extracted with CH$_2$Cl$_2$. The combined organic layers were concentrated in vacuo, and the residue was partitioned between EtOAc and sat. aq. Na$_2$S$_2$O$_3$. The organic layer was then washed successively with H$_2$O and brine, dried over MgSO$_4$, filtered, and concentrated in vacuo. Purification by column chromatography (40:60 to 50:50 EtOAc/hexanes) provided 4-methyl-N-(3-oxopropyl)benzenesulfonamide (0.903 g, 3.97 mmol, 79% yield) as a yellow oil.

Analytical data for II: $^1$H NMR (500 MHz, CDCl$_3$) δ 9.73 (s, 1H), 7.74 (d, J=8.3 Hz, 2H), 7.32 (d, J=8.0 Hz, 2H), 4.92 (t, J=6.6 Hz, 1H), 3.21 (q, J=6.1 Hz, 2H), 2.75 (t, J=5.8 Hz, 2H), 2.43 (s, 3H). $^1$H NMR data for this product corresponds with literature values.

Example 3

Methyl (E)-5-((4-methylphenyl)sulfonamido)pent-2-enoate (III)

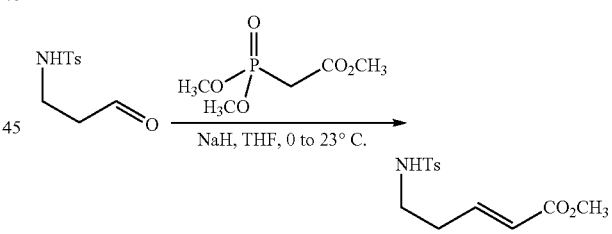

To a cooled (0° C.) solution of methyl 2-(dimethoxyphosphoryl)acetate (8.8 mL, 54.4 mmol) in THF (253 mL) was added sodium hydride (6.73 g, 280 mmol, 5.15 equiv) portion-wise. The resulting thick white reaction mixture was stirred for 60 min, then a solution of 4-methyl-N-(3-oxopropyl)benzenesulfonamide (9.89 g, 43.5 mmol, 0.80 equiv) in THF (110 mL, 0.12 M overall) was added via cannula. Upon completion of the reaction, H$_2$O was added to quench, and the organic solvent was removed in vacuo. The remaining aqueous mixture was extracted with EtOAc, and the combined organic layers were dried over MgSO$_4$, filtered, and concentrated in vacuo. Purification by column chromatography (20:20:60 to 25:25:50 CH$_2$Cl$_2$/Et$_2$O/hexanes) provided methyl (E)-5-((4-methylphenyl)sulfonamido)pent-2-enoate (7.73 g, 27.3 mmol, 63% yield) as a yellow oil.

Analytical Data for III: $^1$H NMR (500 MHz, CDCl$_3$) δ 7.72 (d, J=8.0 Hz, 2H), 7.30 (d, J=8.0 Hz, 2H), 6.75 (dt, J=15.7, 7.0 Hz, 1H), 5.79 (d, J=15.7 Hz, 1H), 4.42 (t, J=6.5 Hz, 1H), 3.70 (s, 3H), 3.08 (q, J=6.5 Hz, 2H), 2.42 (s, 3H), 2.36 (qd, J=7.0, 1.5 Hz, 2H). $^1$H NMR data for this product corresponds with literature values.

Example 4

Methyl (E)-5-((4-methyl-N-(3-oxobutyl)phenyl)sulfonamido)pent-2-enoate (16)

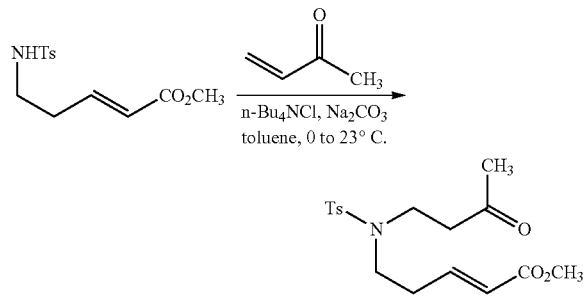

To a cooled (0° C.) solution of (E)-methyl 5-(4-methyl-phenylsulfonamido)pent-2-enoate (11.4 g, 32.2 mmol) in toluene (80 mL, 0.4 M) was added tetrabutylammonium chloride (1.20 g, 4.93 mmol, 0.15 equiv) and sodium carbonate (7.82 g, 73.7 mmol, 2.3 equiv). Methyl vinyl ketone (3.87 ml, 47.7 mmol, 1.5 equiv) was then added drop-wise, and the reaction was allowed to warm to ambient temperature. Upon completion of the reaction (18 h; monitored by TLC), sat. aq. NH$_4$Cl was added, and the mixture was extracted with EtOAc (3×). The combined organic layers were washed with brine, dried over MgSO$_4$, filtered, and concentrated in vacuo. Purification by column chromatography (25:25:50 CH$_2$Cl$_2$/Et$_2$O/hexanes) provided (E)-methyl 5-(4-methyl-N-(3-oxobutyl) phenylsulfonamido)pent-2-enoate (9.46 g, 26.8 mmol, 83% yield) as a pale yellow oil.

Analytical data for 16: IR (film) 2951, 1714, 1658, 1598 cm$^{-1}$; $^1$H NMR (500 MHz, CDCl$_3$) δ 7.65 (d, J=8.3 Hz, 2H), 7.29 (d, J=8.0 Hz, 2H), 6.80 (dt, J=15.8, 7.0 Hz, 1H), 5.82 (d, J=15.7 Hz, 1H), 3.71 (s, 3H), 3.31 (t, J=7.1 Hz, 2H), 3.20 (dd, J=8.3, 6.6 Hz, 2H), 2.81 (t, J=7.1 Hz, 2H), 2.45-2.39 (m, 5H), 2.13 (s, 3H). $^{13}$C NMR (125 MHz, CDCl$_3$) δ 206.9, 166.6, 144.7, 143.8, 135.9, 129.9, 127.3, 123.3, 51.7, 48.2, 43.8, 43.6, 31.8, 30.4, 21.6; HRMS (ESI): Mass calcd for C$_{17}$H$_{24}$NO$_5$S [M+H]$^+$=354.1375; found 354.1365.

Example 5

Methyl 2-((3R,4R)-3-acetyl-1-tosylpiperidin-4-yl)acetate (15)

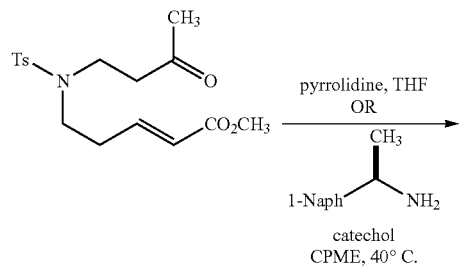

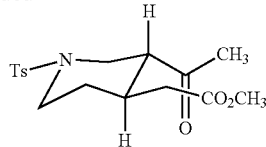

Racemate:

To a solution of (E)-methyl 5-(4-methyl-N-(3-oxobutyl)phenylsulfonamido)pent-2-enoate (0.977 g, 2.76 mmol) in THF (14 mL, 0.2 M) was added pyrrolidine (57 µL, 0.69 mmol, 0.25 equiv). The resulting mixture was stirred at ambient temperature under inert atmosphere until SM was consumed (48 h; monitored by TLC). Solvent was then removed in vacuo, and the residue purified by column chromatography (35:65 EtOAc/hexanes) to obtain racemic methyl 2-((3R,4R)-3-acetyl-1-tosylpiperidin-4-yl)acetate (0.965 g, 2.73 mmol, 99% yield, >95:5 dr) as a colorless solid.

Enantioselective Process:

To a solution of (E)-methyl 5-(4-methyl-N-(3-oxobutyl)phenylsulfonamido)pent-2-enoate (0.177 g, 0.500 mmol) and catechol (0.055 g, 0.50 mmol, 1.0 equiv) in CPME (0.50 mL, 1.0 M) was added (R)-1-(naphthalen-1-yl)ethanamine (24 µL, 0.15 mmol, 0.30 equiv). The resulting mixture was stirred at 40° C. under inert atmosphere for 48 h. Reaction mixture was diluted with EtOAc, then washed successively with 10% aq. AcOH, sat. aq. NaHCO$_3$, and brine. The organic layer was then dried over Na$_2$SO$_4$, filtered, and concentrated in vacuo. Purification by column chromatography (20:80 EtOAc/hexanes) followed by trituration with Et$_2$O provided methyl 2-((3R,4R)-3-acetyl-1-tosylpiperidin-4-yl)acetate (0.140 g, 0.396 mmol, 79% yield, >95:5 dr) as a colorless solid. Enantiomeric ratio was measured by chiral phase HPLC (Chiralcel OD-H, 5%, i-PrOH/Hexanes, 1.0 mL/min, 210 nm), Rt$_1$ (minor)=61.9 min, Rt$_2$ (major)=83.1 min; er>99:1.

Analytical data for 15: [α]$_D^{25}$: 26.0° (c 0.10, CHCl$_3$); IR (film) 1728, 1703, 1440 cm$^{-1}$; $^1$H NMR (500 MHz, CDCl$_3$) δ 7.61 (d, J=7.9 Hz, 2H), 7.32 (d, J=8.0 Hz, 2H), 3.83 (ddd, J=11.6, 3.9, 1.9 Hz, 1H), 3.72 (d, J=11.6 Hz, 1H), 3.63 (s, 3H), 2.74 (td, J=10.7, 3.9 Hz, 1H), 2.44 (s, 3H), 2.32-2.26 (m, 2H), 2.25 (s, 3H), 2.23-2.10 (m, 2H), 2.09-2.00 (m, 1H), 1.91-1.83 (m, 1H), 1.44 (dtd, J=13.4, 11.9, 4.3 Hz, 1H). $^{13}$C NMR (125 MHz, CDCl$_3$) δ 208.8, 172.0, 144.1, 132.8, 130.0, 127.8, 53.4, 51.8, 48.0, 46.1, 37.9, 33.7, 31.1, 29.7, 21.7; HRMS (ESI): Mass calcd for C$_{17}$H$_{24}$NO$_5$S [M+H]$^+$=354.1375; found 354.1370.

Example 6

Methyl 2-((3R,4R)-3-((S)-1-hydroxyethyl)-1-tosylpiperidin-4-yl)acetate (17)

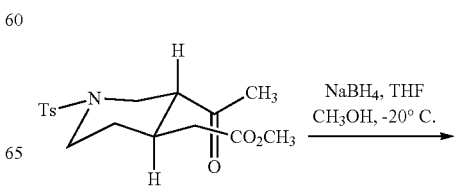

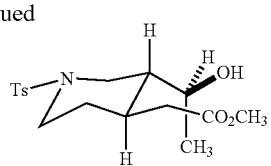

To a −20° C. solution of methyl 2-((3R,4R)-3-acetyl-1-tosylpiperidin-4-yl)acetate (3.86 g, 10.9 mmol) in 50:50 THF/MeOH (110 mL, 0.1 M) was added NaBH$_4$ (2.066 g, 54.6 mmol, 5.0 equiv). The reaction mixture was kept at −20° C. (undesired side products form at temperatures above −10° C.) until completion of reaction (2 h; monitored by TLC), whereupon the reaction was quenched with sat. aq. NaHCO$_3$, diluted with CH$_2$Cl$_2$, and allowed to slowly warm to ambient temperature. The separated aqueous layer was further extracted with dichloromethane (3×). The combined organic layers were dried over Na$_2$SO$_4$ and concentrated in vacuo. Purification by flash chromatography (33:33:33 CH$_2$Cl$_2$/Et$_2$O/hexanes) provided methyl 2-((3R,4R)-3-((S)-1-hydroxyethyl)-1-tosylpiperidin-4-yl)acetate (3.75 g, 10.55 mmol, 97% yield, >95:5 dr) as a colorless oil.

Analytical data for 17: $[\alpha]_D^{25}$: 22.0° (c 0.10, CHCl$_3$); IR (film) 3517, 2921, 1732, 1598, 1438 cm$^{-1}$; $^1$H NMR (500 MHz, CDCl$_3$) δ 7.63 (d, J=8.3 Hz, 2H), 7.31 (d, J=8.0 Hz, 2H), 3.90 (dq, J=6.9, 3.8 Hz, 1H), 3.72-3.68 (m, 1H), 3.67 (s, 3H), 3.66-3.61 (m, 1H), 2.60 (s, 1H), 2.46 (dd, J=17.0, 7.1 Hz, 1H), 2.43 (s, 3H), 2.38 (dd, J=11.8, 10.4 Hz, 1H), 2.33 (td, J=11.6, 3.1 Hz, 1H), 2.24 (dd, J=17.0, 4.8 Hz, 1H), 1.89 (ddd, J=17.2, 9.1, 5.7 Hz, 1H), 1.76 (dq, J=13.3, 3.6 Hz, 1H), 1.51 (dtd, J=13.2, 11.4, 4.2 Hz, 1H), 1.35 (tt, J=10.3, 3.4 Hz, 1H), 1.23 (d, J=6.5 Hz, 3H). $^{13}$C NMR (125 MHz, CDCl$_3$) (174.5, 143.7, 133.1, 129.8, 127.8, 65.3, 52.2, 47.5, 46.0, 44.9, 38.3, 32.4, 31.5, 21.7, 20.3; HRMS (ESI): Mass calcd for C$_{17}$H$_{26}$NO$_5$S [M+H]$^+$=356.1532; found 356.1535.

Example 7

(1S,4aR,8aR)-1-methyl-7-tosyloctahydro-3H-pyrano[3,4-c]pyridin-3-one (18)

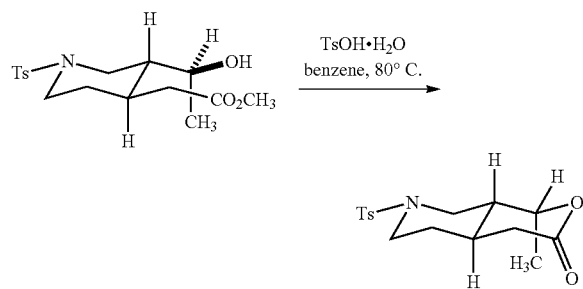

To a solution of methyl 2-((3R,4R)-3-((S)-1-hydroxyethyl)-1-tosylpiperidin-4-yl)acetate (1.04 g, 2.93 mmol) in benzene (19.5 mL, 0.15 M) was added TsOH·H$_2$O (0.084 g, 0.440 mmol, 0.15 equiv). The reaction was heated to reflux until completion of reaction (11 h; monitored by TLC and LCMS), whereupon the reaction was cooled to room temperature and successively washed with sat. aq. NaHCO$_3$ and water. The aqueous washes were extracted with EtOAc (3×), and the combined organic layers were dried over Na$_2$SO$_4$ and concentrated in vacuo. Purification by flash chromatography (50:50 EtOAc/hexanes) provided (1S,4aR,8aR)-1-methyl-7-tosyloctahydro-3H-pyrano[3,4-c]pyridin-3-one (0.648 g, 2.01 mmol, 68% yield) as a colorless oil.

Analytical data for 18: $[\alpha]_D^{25}$: −18.0° (c 0.10, CHCl$_3$); IR (film) 2924, 1724, 1596, 1445 cm$^{-1}$; $^1$H NMR (500 MHz, CDCl$_3$) δ 7.64 (d, J=8.3 Hz, 2H), 7.34 (d, J=8.0 Hz, 2H), 4.71-4.62 (m, 1H), 3.83 (dddd, J=30.4, 11.1, 4.1, 2.0 Hz, 2H), 2.69 (dd, J=18.2, 5.7 Hz, 1H), 2.44 (s, 3H), 2.25 (td, J=12.2, 2.6 Hz, 1H), 2.15-2.03 (m, 2H), 1.98 (t, J=11.2 Hz, 1H), 1.86 (ddt, J=13.3, 4.8, 2.7 Hz, 1H), 1.73 (qdd, J=11.6, 5.8, 4.1 Hz, 1H), 1.41 (tdd, J=12.8, 11.3, 4.5 Hz, 1H), 1.19 (d, J=6.8 Hz, 3H). $^{13}$C NMR (125 MHz, CDCl$_3$) δ 169.3, 144.1, 133.3, 130.0, 127.7, 76.6, 47.2, 45.9, 39.5, 36.1, 31.6, 28.7, 21.7, 17.5; HRMS (ESI): Mass calcd for C$_{16}$H$_{22}$NO$_4$S [M+H]$^+$=324.1270; found 324.1267.

Example 8

Methyl 2-((3R,4R)-3-((S)-1-((methylsulfonyl)oxy)ethyl)-1-tosylpiperidin-4-yl)acetate (17a)

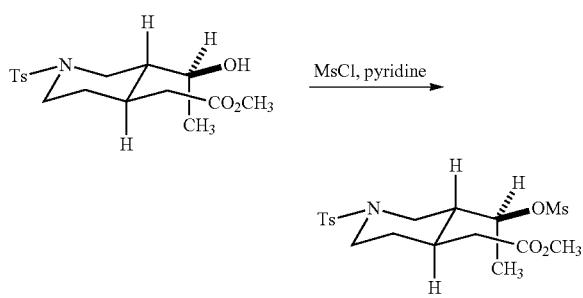

To a solution of methyl 2-((3R,4R)-3-((S)-1-hydroxyethyl)-1-tosylpiperidin-4-yl)acetate (1.37 g, 3.87 mmol) in anhydrous pyridine (15.5 mL, 0.25 M) was added methanesulfonyl chloride (0.45 mL, 5.80 mmol, 1.50 equiv). The resulting solution went from yellow to a pale orange color with white precipitate, and was stirred at ambient temperature under inert atmosphere. Upon completion of the reaction (16 h; monitored by LCMS), pyridine was removed in vacuo, and the residue was partitioned between CH$_2$Cl$_2$ and sat. aq. NaHCO$_3$.

The aqueous layer was further extracted with CH$_2$Cl$_2$ (3×), and the combined organic layers were washed successively with sat. aq. CuSO$_4$ and brine, dried over Na$_2$SO$_4$, filtered, and concentrated in vacuo to provide methyl 2-((3R,4R)-3-((S)-1-((methylsulfonyl)oxy)ethyl)-1-tosylpiperidin-4-yl)acetate (1.49 g, 3.43 mmol, 89% yield) as a yellow foam, which was used without further purification.

Analytical data for 17a: $[\alpha]_D^{25}$: 34.0° (c 0.10, CHCl$_3$); IR (film) 2943, 1732, 1598, 1438 cm$^{-1}$; $^1$H NMR (500 MHz, Acetone-d6) δ 7.69 (d, J=8.3 Hz, 2H), 7.45 (d, J=8.0 Hz, 2H), 5.07 (qd, J=6.5, 2.9 Hz, 1H), 3.76 (ddd, J=11.7, 3.7, 1.8 Hz, 1H), 3.61 (s, 3H), 3.60-3.56 (m, 1H), 3.10 (s, 3H), 2.78-2.76 (m, 1H), 2.67 (dd, J=15.6, 3.6 Hz, 1H), 2.44 (s, 3H), 2.38 (td, J=11.7, 2.8 Hz, 1H), 2.34-2.27 (m, 2H), 1.91-1.83 (m, 2H), 1.80 (tt, J=10.0, 3.3 Hz, 1H), 1.47 (d, J=6.5 Hz, 3H). $^{13}$C NMR (125 MHz, Acetone-d6) δ 173.0, 144.7, 134.5, 130.8, 128.8, 78.1, 51.8, 46.6, 46.0, 45.1, 38.9, 37.3, 33.6, 30.8, 21.6, 19.1. HRMS (ESI): Mass calcd for C$_{18}$H$_{28}$NO$_7$S$_2$ [M+H]$^+$=434.1307; found 434.1296.

Example 9

Methyl (R,Z)-2-(3-ethylidene-1-tosylpiperidin-4-yl)acetate (19)

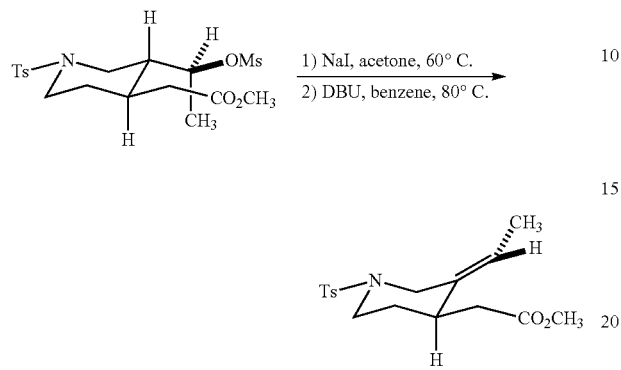

To a solution of methyl 2-((3R,4R)-3-((S)-1-((methylsulfonyl)oxy)ethyl)-1-tosylpiperidin-4-yl)acetate (1.48 g, 3.42 mmol) in acetone (17 mL, 0.2 M) was added sodium iodide (2.05 g, 13.7 mmol, 4.00 equiv). The resulting solution was heated to 60° C. under inert atmosphere while being shielded from light. Upon completion of the iodination reaction (48 h; monitored by LCMS), the reaction was cooled to ambient temperature, and the solvent was removed in vacuo. The residue was partitioned between $CH_2Cl_2$ and sat. aq. $NaHCO_3$. The separated organic layer was washed with sat. aq. $Na_2S_2O_3$ (2×), water, and brine. The organic layer was then dried over $Na_2SO_4$, filtered, and concentrated in vacuo to afford the alkyl iodide as an orange foam which was used without further purification.

The unpurified alkyl iodide was then dissolved in anhydrous benzene (68.0 mL, 0.05 M). DBU (0.62 mL, 4.11 mmol, 1.20 equiv) was added, and the resulting solution was heated to 80° C. while being shielded from light. Upon completion of the elimination reaction (41 h; monitored by LCMS), the reaction was cooled to ambient temperature, and the solvent was removed in vacuo. The residue was then dissolved in toluene and washed with $H_2O$ (2×). The combined aqueous layers were then extracted with toluene (3×). The combined organic layers were washed successively with 10% HCl and brine, dried over $Na_2SO_4$, filtered, and concentrated in vacuo. Purification by column chromatography (25:75 EtOAc/hexanes) provided methyl (R,Z)-2-(3-ethylidene-1-tosylpiperidin-4-yl)acetate (0.900 g, 2.67 mmol, 78% yield) as a colorless solid.

Analytical data for 19: $[\alpha]_D^{25}$: 64.5° (c 0.11, $CHCl_3$); IR (film) 2945, 2822, 1734, 1597, 1496, 1457, 1430 cm$^{-1}$; $^1$H NMR (500 MHz, $CDCl_3$) δ 7.67 (d, J=8.3 Hz, 2H), 7.32 (d, J=8.0 Hz, 2H), 5.30-5.25 (m, 1H), 4.05 (d, J=12.6 Hz, 1H), 3.63 (s, 3H), 3.42 (dtd, J=11.5, 4.1, 2.0 Hz, 1H), 3.18 (d, J=12.6 Hz, 1H), 2.85 (ddd, J=12.3, 9.3, 3.5 Hz, 1H), 2.48 (dd, J=10.4, 7.0 Hz, 2H), 2.44 (s, 3H), 2.28-2.19 (m, 1H), 1.82 (ddt, J=13.3, 5.9, 3.8 Hz, 1H), 1.68 (d, J=6.8 Hz, 3H), 1.41 (dtd, J=13.0, 9.0, 3.9 Hz, 1H). $^{13}$C NMR (125 MHz, $CDCl_3$) δ 172.8, 143.7, 133.5, 133.4, 129.8, 127.9, 119.6, 51.8, 45.5, 45.2, 38.0, 36.8, 31.7, 21.7, 13.2. HRMS (ESI): Mass calcd for $C_{17}H_{24}NO_4S$ [M+H]$^+$=338.1426; found 338.1422.

Example 10

(R,Z)-Benzyl 3-ethylidene-4-(2-methoxy-2-oxoethyl)piperidine-1-carboxylate (20)

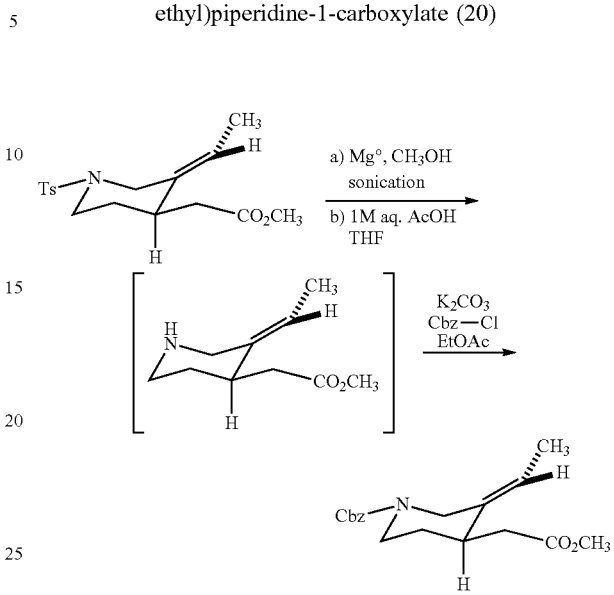

To a flask containing (R,Z)-2-(3-ethylidene-1-tosylpiperidin-4-yl)acetate (0.200 g, 0.593 mmol) and magnesium powder (0.144 g, 5.93 mmol, 10.0 equiv) was added anhydrous methanol (5.93 mL, 0.100 M). The resulting mixture was sonicated at ambient temperature for 2.5 h, whereupon more magnesium powder (0.144 g, 5.93 mmol, 10.0 equiv) was added and the suspension was sonicated until completion of de-protection (4.5 h total; monitored by TLC and LCMS). The solvent was removed in vacuo, and the residue suspended in 1 M aq. AcOH (7.1 mL, 7.1 mmol, 12.0 equiv) and an equal volume of THF (7.1 mL). The biphasic mixture was stirred vigorously for 30 min, and then diluted with EtOAc (44 mL, 0.01 M overall). $K_2CO_3$ (1.23 g, 8.89 mmol, 15.0 equiv) and benzyl chloroformate (1.27 mL, 8.89 mmol, 15.0 equiv) were then added, and the resulting mixture was stirred at ambient temperature for 18 h (reaction progress monitored by LCMS). Reaction mixture was partitioned between EtOAc and sat. aq. Rochelle's salt. The aqueous layer was further extracted with EtOAc, and the combined organic layers were washed with sat. aq. $NaHCO_3$, dried over $Na_2SO_4$, filtered, and concentrated in vacuo. Purification by column chromatography (3:27:70 acetone/$CH_2Cl_2$/hexanes) provided methyl (R,Z)-benzyl 3-ethylidene-4-(2-methoxy-2-oxoethyl)piperidine-1-carboxylate (0.132 g, 0.416 mmol, 70% yield) as a colorless oil.

Analytical data for 20: $[\alpha]_D^{25}$: 14.0° (c 0.10, $CHCl_3$); IR (film) 2945, 2861, 1736, 1697, 1497, 1432 cm$^{-1}$; $^1$H NMR (500 MHz, $CDCl_3$) δ 7.40-7.28 (m, 5H), 5.25 (br s, 1H), 5.16-5.09 (m, 2H), 4.42 (br d, J=14.3 Hz, 1H), 3.81 (br s, 1H), 3.70 (br d, J=15.6 Hz, 1H), 3.67 (s, 3H), 3.34 (ddd, J=13.5, 9.2, 3.6 Hz, 1H), 2.78-2.64 (m, 1H), 2.59 (dd, J=15.1, 7.1 Hz, 1H), 2.34 (dd, J=15.1, 7.8 Hz, 1H), 1.84-1.56 (m, 4H), 1.43-1.32 (m, 1H). $^{13}$C NMR (125 MHz, $CDCl_3$) δ 173.0, 155.2, 137.1, 135.4, 135.2, 128.6, 128.1, 128.0, 118.6, 118.2, 67.2, 51.8, 43.5, 43.2, 38.5, 37.2, 32.3, 13.1. HRMS (ESI): Mass calcd for $C_{18}H_{24}NO_4$ [M+H]$^+$ 318.1705; found 318.1693.

Example 11

(1S,4aR,8aS)-benzyl 1-methyl-3-oxohexahydro-1H-pyrano[3,4-c]pyridine-7(3H)-carboxylate (21)

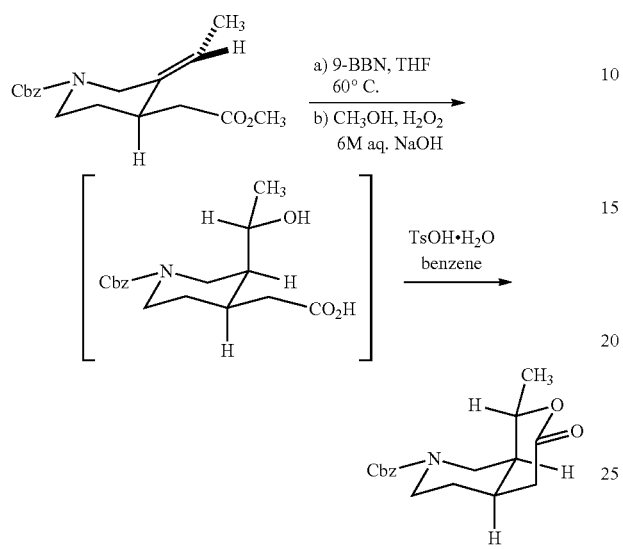

To a cooled (0° C.) solution of (R,Z)-benzyl 3-ethylidene-4-(2-methoxy-2-oxoethyl)piperidine-1-carboxylate (95 mg, 0.300 mmol) in THF (1.85 mL, 0.16 M) was added a freshly prepared 0.78 M solution of 9-BBN in THF (1.15 mL, 0.900 mmol, 3.00 equiv). The resulting mixture was heated to 40° C. for 16 h (consumption of alkene monitored by TLC), whereupon the mixture was cooled back down to 0° C. Methanol (1.2 mL) was added drop-wise, followed by 6.0 M aq. NaOH (0.75 mL, 4.50 mmol, 15.0 equiv) and 30% aq. H$_2$O$_2$ (0.46 mL, 4.50 mmol, 15.0 equiv). The resulting suspension was stirred at 0° C. for 2 h, diluted with water, and extracted with CH$_2$Cl$_2$ (3×). The DCM extracts were discarded, then the aqueous layer was acidified to pH~1 with 10% aq. HCl and extracted (3×) with EtOAc. The combined EtOAc extracts were dried over Na$_2$SO$_4$, filtered, and concentrated in vacuo to provide a mixture of the hydroxy-acid and lactone product.

The unpurified mixture was then dissolved in benzene (3.0 mL, 0.1 M) and to this solution was added TsOH·H$_2$O (57 mg, 0.300 mmol, 1.0 equiv). The resulting solution was stirred at ambient temperature for 12 h. The reaction was then partitioned between EtOAc and sat. aq. NaHCO$_3$. Extracted aqueous layer with EtOAc (3×), and the combined organic layers were dried over Na$_2$SO$_4$, filtered, and concentrated in vacuo. Purification by column chromatography (4:96 acetone/DCM) provided (1 S,4aR,8aS)-benzyl 1-methyl-3-oxohexahydro-1H-pyrano[3,4-c]pyridine-7(3H)-carboxylate (46 mg, 0.152 mmol, 51% yield) as a colorless oil.

Analytical data for 21: [α]$_D^{25}$: 20.3° (c 0.30, CHCl$_3$); IR (film) 2926, 1729, 1691, 1431 cm$^{-1}$; $^1$H NMR (500 MHz, CDCl$_3$) δ 7.40-7.30 (m, 5H), 5.17 (br d, J=13.2 Hz, 1H), 5.08 (br d, J=12.6 Hz, 1H), 4.44 (t, J=8.2 Hz, 1H), 4.22-3.98 (m, 2H), 3.14 (dd, J=14.0, 3.6 Hz, 1H), 3.08-2.88 (m, 1H), 2.66 (dd, J=17.7, 6.6 Hz, 1H), 2.44 (dd, J=17.7, 3.9 Hz, 1H), 2.18 (ddd, J=11.3, 5.5, 3.1 Hz, 1H), 1.91-1.57 (m, 2H), 1.51-1.32 (m, 3H). $^{13}$C NMR (125 MHz, CDCl$_3$) δ 170.2, 155.5, 136.4, 128.6, 128.3, 128.2, 75.2, 74.9, 67.5, 44.1, 43.8, 43.2, 38.6, 35.2, 31.0, 27.6, 20.8, 20.5, 19.8, 17.9; HRMS (ESI); Mass calcd for C$_{17}$H$_{21}$NNaO$_4$ [M+Na]$^+$=326.1363; found 326.1369.

Example 12

Methyl (1S,4aS,8aR)-1-methyl-7-tosyl-4a,5,6,7,8,8a-hexahydro-1H-pyrano[3,4-c]pyridine-4-carboxylate (23)

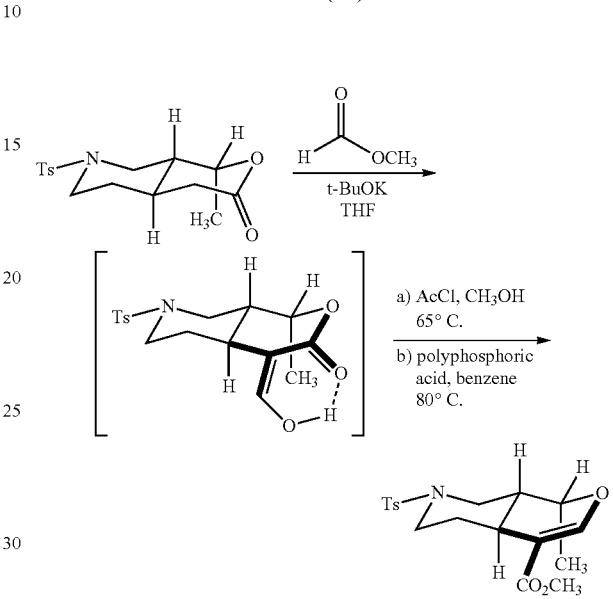

A solution of potassium tert-butoxide (0.193 g, 1.72 mmol, 5.0 equiv) in THF (1.72 mL) was added to a solution of (1S,4aR,8aR)-1-methyl-7-tosyloctahydro-3H-pyrano[3,4-c]pyridin-3-one (111 mg, 0.344 mmol) in THF (1.72 mL; 0.1 M overall). After 2 h, methyl formate (0.32 mL, 5.16 mmol, 15.0 equiv) was added drop-wise and the resulting mixture was allowed to stir until reaction was complete (12 h; monitored by TLC and LCMS). Reaction was then quenched with 10% aq. AcOH, then this mixture was partitioned between CH$_2$Cl$_2$ and sat. aq. NaHCO$_3$. The aqueous layer was further extracted with CH$_2$Cl$_2$, and the combined organic layers were dried over Na$_2$SO$_4$, filtered, and concentrated in vacuo to afford the α-formyl lactone as a yellow oil which was used without further purification.

The unpurified α-formyl lactone was dissolved in methanol (2.3 mL), and to this mixture was added a solution of acetyl chloride (0.22 mL, 3.11 mmol, 10.0 equiv) in methanol (2.3 mL, 0.067 M overall). The resulting mixture was then heated to 65° C. until the α-formyl lactone was consumed (15 h; monitored by TLC and LCMS). The solvent was removed in vacuo, and the residue was then re-dissolved in benzene (2.7 mL, 0.12 M). Polyphosphoric acid (10 mg) was added, and the mixture was heated to 80° C. for 2 h (reaction progress monitored by LCMS). After allowing reaction to cool to ambient temperature, the mixture was partitioned between CH$_2$Cl$_2$ and sat. aq. NaHCO$_3$. The aqueous layer was further extracted with CH$_2$Cl$_2$, and the combined organic layers were dried over Na$_2$SO$_4$, filtered, and concentrated in vacuo. Purification by column chromatography (20:80 EtOAc/hexanes) provided methyl (1S,4aS, 8aR)-1-methyl-7-tosyl-4a,5,6,7,8,8a-hexahydro-1H-pyrano [3,4-c]pyridine-4-carboxylate (84 mg, 0.230 mmol, 67% yield) as a colorless foam.

Analytical data for 23: $[\alpha]_D^{25}$: 80.0° (c 0.10, CHCl$_3$); IR (film) 2925, 1704, 1615, 1435 cm$^{-1}$; $^1$H NMR (500 MHz, CDCl$_3$) δ 7.65 (d, J=8.3 Hz, 2H), 7.45 (d, J=1.7 Hz, 1H), 7.34 (d, J=8.0 Hz, 3H), 4.37 (qd, J=6.6, 3.4 Hz, 1H), 3.88 (ddt, J=11.9, 4.4, 2.4 Hz, 1H), 3.76 (dt, J=9.8, 2.1 Hz, 1H), 3.67 (s, 3H), 2.72 (dd, J=13.3, 2.9 Hz, 1H), 2.45 (s, 3H), 2.34 (td, J=12.2, 2.8 Hz, 1H), 2.05-1.89 (m, 3H), 1.34-1.22 (m, 1H), 1.04 (d, J=6.6 Hz, 3H). $^{13}$C NMR (125 MHz, CDCl$_3$) δ 167.1, 154.3, 143.9, 133.2, 129.9, 127.8, 106.7, 73.0, 51.1, 48.0, 46.6, 40.7, 30.3, 28.7, 21.7, 14.8. HRMS (ESI): Mass calcd for C$_{18}$H$_{24}$NO$_5$S [M+H]$^+$=366.1375; found 366.1371.

Example 13

(1S,4aS,8aR)-methyl 1-methyl-4a,5,6,7,8,8a-hexahydro-1H-pyrano[3,4-c]pyridine-4-carboxylate (12)

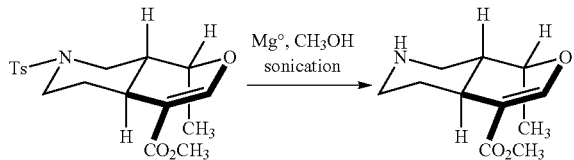

To a vial containing (1S,4aS,8aR)-methyl 1-methyl-7-tosyl-4a,5,6,7,8,8a-hexahydro-1H-pyrano[3,4-c]pyridine-4-carboxylate (27.7 mg, 0.076 mmol) and magnesium powder (18.4 mg, 0.758 mmol, 10.0 equiv) was added anhydrous methanol (0.76 mL, 0.10 M). The resulting mixture was sonicated at ambient temperature for 2.5 h whereupon more magnesium powder (18.4 mg, 0.758 mmol, 10.0 equiv) was added and the suspension was sonicated until completion of de-protection (3.5 h total; monitored by TLC and LCMS). The reaction mixture was then poured into sat. aq. NH4Cl at 0° C. and the resulting mixture extracted with CH2Cl2 (3×). The combined organic layers were dried, filtered, and concentrated in vacuo to provide (1S,4aS,8aR)-methyl 1-methyl-4a,5,6,7,8,8a-hexahydro-1H-pyrano[3,4-c]pyridine-4-carboxylate (13.4 mg, 0.057 mmol, 75% yield) as a colorless amorphous solid which was used without further purification.

Analytical Data for 12: $[\alpha]_D^{25}$: 83.6° (c 0.11, CHCl$_3$); IR (film) 2921, 1700, 1614, 1436 cm$^{-1}$; H NMR (500 MHz, CDCl$_3$) δ 7.46 (d, J=1.8 Hz, 1H), 4.31 (qd, J=6.6, 4.0 Hz, 1H), 3.69 (s, 3H), 3.14 (dt, J=12.7, 3.1 Hz, 1H), 2.98 (dd, J=11.7, 3.1 Hz, 1H), 2.72 (td, J=12.5, 2.8 Hz, 1H), 2.62 (dd, J=13.0, 3.0 Hz, 1H), 2.41 (t, J=11.5 Hz, 1H), 2.30-2.22 (m, 1H), 1.76 (tt, J=11.2, 3.6 Hz, 1H), 1.12 (d, J=6.6 Hz, 3H). $^{13}$C NMR (125 MHz, CDCl$_3$) δ 167.5, 154.1, 107.9, 73.7, 51.0, 48.5, 46.9, 42.7, 31.1, 30.8, 14.9. HRMS (ESI): Mass calcd for C$_{11}$H$_{18}$NO$_3$ [M+H]$^+$=212.1287; found 212.1281.

Example 14

2,3-Secoajmalicine (24)

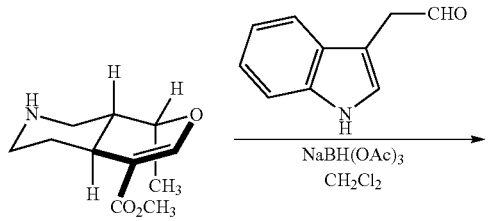

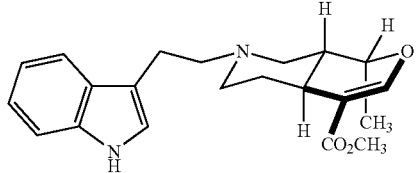

Preparation of 2-(1H-indol-3-yl)acetaldehyde

To a solution of tryptophol (89 mg, 0.550 mmol) in DMSO (2.2 mL, 0.25 M) was added IBX (169 mg, 0.605 mmol, 1.10 equiv). The resulting suspension was stirred under inert atmosphere for 90 min (conversion monitored by GCMS). Reaction then diluted with water (8.8 mL=4× amount of DMSO), filtered through a cotton plug, and the filtrate extracted with Et$_2$O (2×). The combined organic layers were dried over Na$_2$SO$_4$, filtered, and concentrated in vacuo to provide 2-(1H-indol-3-yl)acetaldehyde (64 mg, 0.402 mmol, 73% yield) as a yellow oil. (NOTE: This aldehyde rapidly decomposes and was used in reductive amination immediately after workup)

Analytical data for 2-(1H-indol-3-yl)acetaldehyde $^1$H NMR (500 MHz, CDCl$_3$) δ 9.76 (t, J=2.5 Hz, 1H), 8.39 (s, 1H), 7.54 (dd, J=7.9, 1.1 Hz, 1H), 7.42-7.38 (m, 1H), 7.24-7.21 (m, 1H), 7.17 (d, J=2.3 Hz, 1H), 7.14 (ddd, J=8.0, 7.1, 1.0 Hz, 1H), 3.81 (dd, J=2.5, 0.8 Hz, 2H). $^1$H NMR data for this product corresponds with literature values.

To a solution of (1S,4aS,8aR)-methyl 1-methyl-4a,5,6,7,8,8a-hexahydro-1H-pyrano[3,4-c]pyridine-4-carboxylate (42.5 mg, 0.201 mmol) and 2-(1H-indol-3-yl)acetaldehyde (64 mg, 0.402 mmol, 2.00 equiv) in CH$_2$Cl$_2$ (0.50 mL, 0.4 M) was added sodium triacetoxyborohydride (63.9 mg, 0.302 mmol, 1.50 equiv). The reaction was stirred at ambient temperature until the secondary amine was consumed (2 h; monitored by LCMS). Reaction was then quenched with sat. aq. NaHCO$_3$, the aqueous layer was extracted with CH$_2$Cl$_{12}$, and the combined organic layers were dried over Na$_2$SO$_4$, filtered, and concentrated in vacuo. Purification by column chromatography (20:80 to 40:60 EtOAc/hexanes) followed by preparatory TLC (1:10:89 Et$_3$N/acetone/CHCl$_3$) provided 2,3-secoajmalicine (48 mg, 0.135 mmol, 67% yield) as tan colored foam.

Analytical data for 24: $[\alpha]_D^{25}$: 36.6° (c 0.38, CHCl$_3$); IR (film) 2923, 1697, 1614, 1435 cm$^{-1}$; $^1$H NMR (500 MHz, CDCl$_3$) δ 7.99 (s, 1H), 7.64-7.59 (m, 1H), 7.49 (d, J=1.8 Hz, 1H), 7.36 (dt, J=8.1, 0.9 Hz, 1H), 7.19 (ddd, J=8.1, 6.9, 1.2 Hz, 1H), 7.12 (ddd, J=7.9, 7.0, 1.1 Hz, 1H), 7.04 (d, J=2.3 Hz, 1H), 4.36 (qd, J=6.6, 3.9 Hz, 1H), 3.70 (s, 3H), 3.20 (d, J=11.6 Hz, 1H), 3.00 (t, J=8.4 Hz, 3H), 2.80-2.72 (m, 2H), 2.69 (dd, J=13.1, 3.2 Hz, 1H), 2.22-2.11 (m, 2H), 2.01 (q, J=11.4 Hz, 1H), 1.85 (t, J=10.8 Hz, 1H), 1.42-1.30 (m, 1H), 1.14 (d, J=6.6 Hz, 3H). $^3$C NMR (125 MHz, CDCl$_3$) δ 167.6, 154.3, 136.4, 127.6, 122.2, 121.6, 119.4, 119.0, 114.4, 111.3, 107.6, 74.0, 59.5, 55.6, 54.3, 51.0, 41.1, 30.8, 29.5, 23.1, 15.0. HRMS (ESI): Mass calcd for C$_{21}$H$_{27}$N$_2$O$_3$ [M+H]$^+$=355.2022; found 355.2029.

Example 15

(1S,4aS,8aS)-7-benzyl 4-methyl 1-methyl-5,6,8,8a-tetrahydro-1H-pyrano[3,4-c]pyridine-4,7(4aH)-dicarboxylate (25)

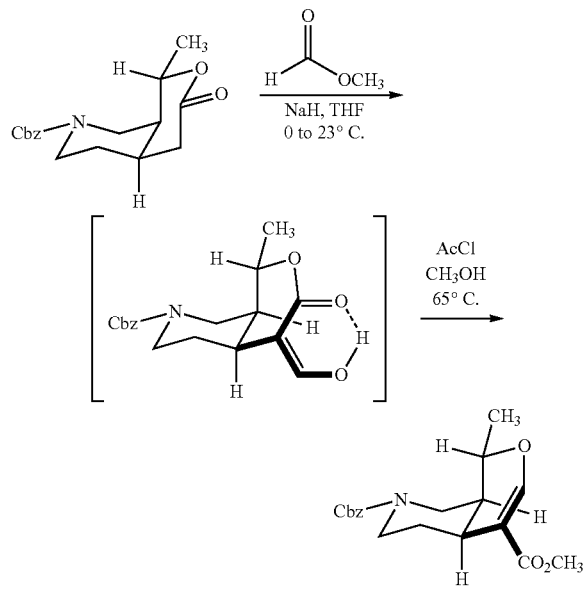

A solution of (1S,4aR,8aS)-benzyl 1-methyl-3-oxohexahydro-1H-pyrano[3,4-c]pyridine-7(3H)-carboxylate (30 mg, 0.099 mmol) in tetrahydrofuran (0.90 mL) was added dropwise to a cooled (0° C.) suspension of oil-free sodium hydride (12 mg, 0.494 mmol, 5.00 equiv) in tetrahydrofuran (0.90 mL; 0.055 M overall). After the resulting suspension was stirred for 1 h at 0° C., methyl formate (0.09 mL, 1.48 mmol, 15.0 equiv) was added. The reaction was allowed to warm to ambient temperature and stir until reaction was complete (18 h; monitored by TLC and LCMS). Reaction was then quenched with 10% aq. AcOH, whereupon reaction mixture became homogeneous, then this mixture was partitioned between CH$_2$Cl$_2$ and sat. aq. NaHCO$_3$. The aqueous layer was further extracted with CH$_2$Cl$_2$, and the combined organic layers were dried over Na$_2$SO$_4$, filtered, and concentrated in vacuo to afford the α-formyl lactone as a yellow oil which was used without further purification.

The unpurified α-formyl lactone was dissolved in methanol (0.74 mL), and to this mixture was added a solution of acetyl chloride (74 μL, 1.04 mmol, 10.5 equiv) in methanol (0.74 mL, 0.067 M overall). The resulting mixture was then heated to 65° C. until reaction was complete (15 h; monitored by TLC and LCMS). The solvent was then removed in vacuo, and residue partitioned between CH$_2$Cl$_2$ and sat. aq. NaHCO$_3$. The aqueous layer was further extracted with CH$_2$Cl$_2$, and the combined organic layers were dried over Na$_2$SO$_4$, filtered, and concentrated in vacuo. Purification by column chromatography (5:95 EtOAc/CH$_2$Cl$_{12}$) provided (1S,4aS,8aS)-7-benzyl 4-methyl 1-methyl-5,6,8,8a-tetrahydro-1H-pyrano[3,4-c]pyridine-4,7(4aH)-dicarboxylate (19 mg, 0.055 mmol, 56% yield) as a colorless oil.

Analytical data for 25: $[\alpha]_D^{25}$: 22.0° (c 0.10, CHCl$_3$); IR (film) 2949, 1694, 1629, 1433 cm$^{-1}$; $^1$H NMR (500 MHz, CDCl$_3$) δ 7.48 (s, 1H), 7.38-7.26 (m, 5H), 5.13 (d, J=12.2 Hz, 1H), 5.06 (d, J=12.2 Hz, 1H), 4.40-4.22 (m, 1H), 4.21-4.03 (m, 2H), 3.68 (s, 3H), 3.06 (br s, 1H), 2.84 (br s, 1H), 2.63 (dt, J=11.8, 4.5 Hz, 1H), 2.06-1.94 (m, 1H), 1.60 (br d, J=29.5 Hz, 1H), 1.44 (br s, 3H), 1.31-1.20 (m, 1H). $^{13}$C NMR (125 MHz, CDCl$_3$) δ 167.6, 155.1, 136.6, 128.5, 128.2, 127.9, 109.6, 71.2, 70.9, 67.3, 51.1, 44.5, 44.0, 37.8, 30.8, 29.4, 19.3, 18.9. HRMS (ESI): Mass calcd for C$_{19}$H$_{23}$NNaO$_5$ [M+Na]$^+$=368.1468; found 368.1473.

Example 16

(1S,4aS,8aS)-methyl 1-methyl-4a,5,6,7,8,8a-hexahydro-1H-pyrano[3,4-c]pyridine-4-carboxylate (11)

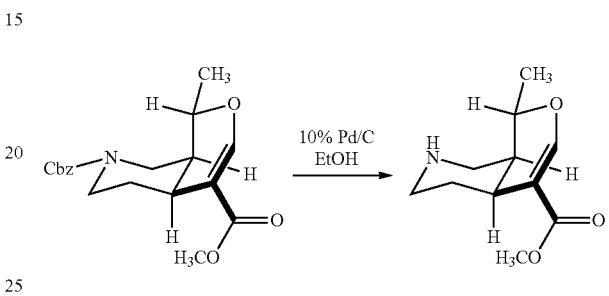

To a solution of (1S,4aS,8aS)-7-benzyl 4-methyl 1-methyl-5,6,8,8a-tetrahydro-1H-pyrano[3,4-c]pyridine-4,7(4aH)-dicarboxylate (35 mg, 0.100 mmol) in anhydrous EtOH (2.0 mL, 0.05 M) was added 10% palladium on carbon (10.6 mg, 0.010 mmol, 0.10 equiv). The suspension was placed under an atmosphere of hydrogen gas and stirred for 2 h (reaction progress monitored by TLC), then filtered through a pad of Celite, which was then rinsed with additional EtOH. The filtrate was concentrated in vacuo to provide (1S,4aS,8aS)-methyl 1-methyl-4a,5,6,7,8,8a-hexahydro-1H-pyrano[3,4-c]pyridine-4-carboxylate (21 mg, 0.099 mmol, 99% yield) as a colorless amorphous solid which was used without further purification.

Analytical data for 11: $[\alpha]_D^{25}$: −43.0° (c 0.10, CHCl$_3$); IR (film) 3340, 2948, 1701, 1629, 1437 cm$^{-1}$; H NMR (500 MHz, CDCl$_3$) 9.64 (s, 1H), 7.53 (s, 1H), 4.57 (dq, J=12.5, 6.4 Hz, 1H), 3.69 (s, 3H), 3.35 (dd, J=13.8, 3.7 Hz, 1H), 3.32-3.25 (m, 1H), 3.15 (dd, J=13.8, 4.7 Hz, 1H), 3.01-2.93 (m, 1H), 2.72 (dt, J=9.6, 4.5 Hz, 1H), 2.24-2.17 (m, 1H), 2.07-1.94 (m, 2H), 1.43 (d, J=6.2 Hz, 3H). $^{13}$C NMR (125 MHz, CDCl$_3$) δ 167.1, 155.6, 107.4, 71.0, 51.4, 43.2, 43.1, 35.6, 28.5, 25.6, 18.7. HRMS (ESI): Mass calcd for C$_{11}$H$_{18}$NO$_3$ [M+H]$^+$=212.1281; found 212.1281.

Example 17

2,3-Secoakuammigine (26)

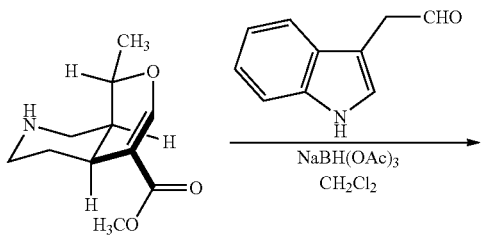

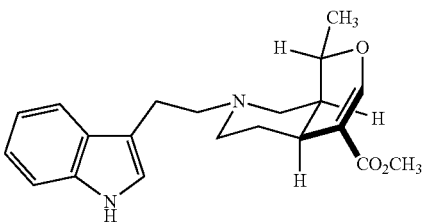

To a solution of (1S,4aS,8aS)-methyl 1-methyl-4a,5,6,7,8,8a-hexahydro-1H-pyrano[3,4-c]pyridine-4-carboxylate (30 mg, 0.141 mmol) and 2-(1H-indol-3-yl)acetaldehyde (45 mg, 0.283 mmol, 2.00 equiv) in CH$_2$Cl$_2$ (0.35 mL, 0.4 M) was added sodium triacetoxyborohydride (45 mg, 0.212 mmol, 1.50 equiv). The reaction was stirred at ambient temperature until the secondary amine was consumed (2 h; monitored by LCMS). Reaction was then quenched with sat. aq. NaHCO$_3$, the aqueous layer was extracted with CH$_2$Cl$_2$, and the combined organic layers were dried over Na$_2$SO$_4$, filtered, and concentrated in vacuo. Purification by column chromatography (15:85 acetone/CH$_2$C$_{12}$) followed by preparatory TLC (1:10:89 Et$_3$N/acetone/CHCl$_3$) provided 2,3-secoakuammigine (33 mg, 0.093 mmol, 66% yield) as a tan foam.

Analytical data for 26: $[\alpha]_D^{25}$: −41.5° (c 0.13, CHCl$_3$); IR (film) 3359, 2926, 1702, 1627, 1456, 1437 cm$^{-1}$; $^1$H NMR (500 MHz, CDCl$_3$) 7.96 (s, 1H), 7.58 (d, J=7.9 Hz, 1H), 7.51 (s, 1H), 7.34 (d, J=8.1 Hz, 1H), 7.17 (t, J=7.5 Hz, 1H), 7.09 (t, J=7.4 Hz, 1H), 7.01 (d, J=2.2 Hz, 1H), 4.46 (dq, J=10.1, 6.3 Hz, 1H), 3.69 (s, 3H), 3.11 (d, J=12.1 Hz, 1H), 2.95-2.82 (m, 5H), 2.65 (ddd, J=12.2, 9.8, 5.8 Hz, 1H), 2.58-2.51 (m, 1H), 2.47 (dt, J=11.8, 4.6 Hz, 1H), 2.27 (dd, J=12.2, 3.4 Hz, 1H), 2.12 (t, J=11.5 Hz, 1H), 2.04 (dt, J=14.5, 3.9 Hz, 1H), 1.31 (d, J=6.3 Hz, 3H). $^{13}$C NMR (125 MHz, CDCl$_3$) δ 168.0, 155.2, 136.2, 127.5, 124.5, 122.0, 121.5, 119.2, 118.8, 114.6, 111.1, 72.4, 59.5, 54.3, 51.0, 38.5, 30.8, 30.2, 29.7, 23.0, 18.4; HRMS (EI): Mass calcd for C$_{21}$H$_{27}$N$_2$O$_3$ [M+H]$^+$=355.2022; found 355.2024.

Example 18

Tetrahydroalstonine (5)

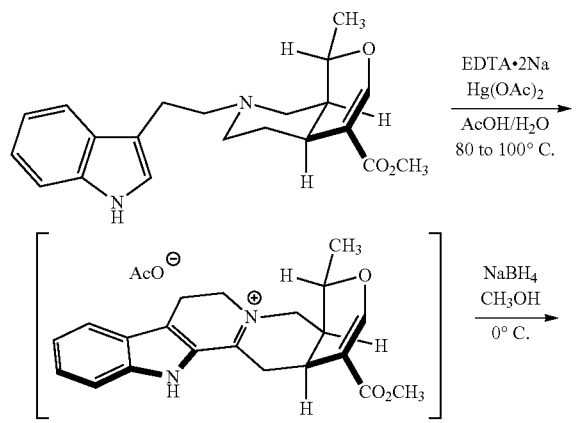

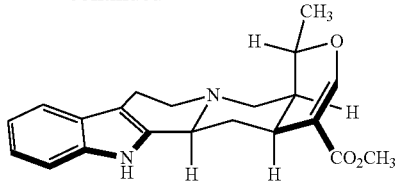

To a solution of 2,3-secoakuammigine (11 mg, 0.031 mmol) in 5% aq. AcOH (0.69 mL, 0.045 M) was added a solution of mercuric acetate (22 mg, 0.068 mmol, 2.20 equiv) and EDTA disodium salt (25 mg, 0.068 mmol, 2.20 equiv) in water (0.69 mL). The resulting solution was kept under inert atmosphere and heated to 80° C. for 4.5 h (reaction progress monitored by LCMS). The reaction was then cooled to 0° C., CH$_3$OH (0.69 mL) was added, and the pH was adjusted to 9 by the addition of 1 M aq. NaOH. To the cold reaction mixture was then added NaBH$_4$ (16 mg, 0.434 mmol, 14.0 equiv), and the reaction stirred at 0° C. for 20 min (reaction progress monitored by LCMS). The excess NaBH$_4$ was then destroyed by drop-wise addition of AcOH. The reaction was then basified to pH 9 with 1 M aq. NaOH, and the mixture was extracted with CH$_2$Cl$_2$ (×5). The combined organic layers were dried over Na$_2$SO$_4$, filtered, and concentrated in vacuo. Purification by preparatory TLC (20:80 EtOAc/hexanes) provided tetrahydroalstonine (4.5 mg, 0.013 mmol, 41% yield) as a colorless amorphous solid.

Analytical data for 5: $[\alpha]_D^{25}$: −86.0° (c 0.10, CHCl$_3$); IR (film) 3358, 2923, 2852, 1703, 1629, 1454, 1438 cm$^{-1}$; $^1$H NMR (500 MHz, CDCl$_3$) δ 7.79 (s, 1H), 7.56 (s, 1H), 7.45 (d, J=7.7 Hz, 1H), 7.28 (d, J=8.0 Hz, 1H), 7.12 (ddd, J=8.0, 7.1, 1.3 Hz, 1H), 7.07 (td, J=7.5, 1.1 Hz, 1H), 4.50 (dq, J=10.3, 6.2 Hz, 1H), 3.75 (s, 3H), 3.36 (dd, J=11.6, 2.4 Hz, 1H), 3.11 (dd, J=12.3, 2.0 Hz, 1H), 2.99-2.89 (m, 2H), 2.79-2.67 (m, 3H), 2.59-2.53 (m, 1H), 2.52-2.47 (m, 1H), 1.70 (d, J=10.6 Hz, 1H), 1.54 (q, J=12.2 Hz, 1H), 1.41 (d, J=6.2 Hz, 3H). $^{13}$C NMR (125 MHz, CDCl$_3$) δ 168.1, 155.9, 136.1, 134.7, 127.4, 121.6, 119.6, 118.2, 110.9, 109.7, 108.3, 72.6, 60.0, 56.5, 53.7, 51.3, 38.6, 34.4, 31.5, 21.9, 18.7. HRMS (ESI): Mass calcd for C$_{21}$H$_{25}$N$_2$O$_3$ [M+H]$^+$=353.1865; found 353.1867.

Example 19

Ajmalicine (7)

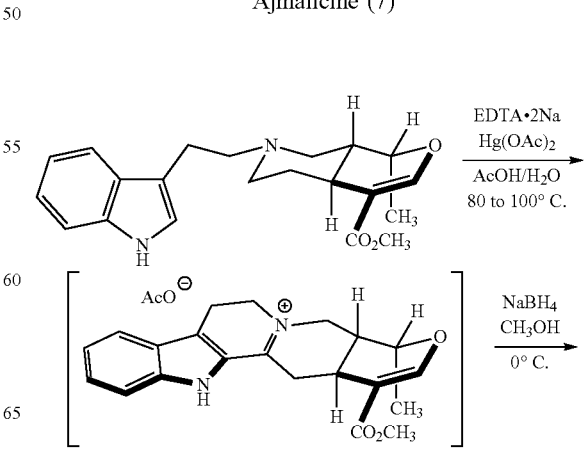

-continued

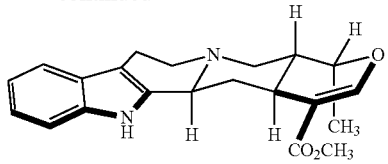

To a solution of 2,3-secoajamlicine (18 mg, 0.051 mmol) in 5% aq. AcOH (1.13 mL, 0.045 M) was added a solution of mercuric acetate (36 mg, 0.112 mmol, 2.20 equiv) and EDTA disodium salt (42 mg, 0.112 mmol, 2.20 equiv) in water (1.12 mL). The resulting solution was kept under inert atmosphere and heated to 80° C. for 4 h, then at 100° C. for 4 h (reaction progress monitored by LCMS). The reaction was then cooled to 0° C., $CH_3OH$ (1.12 mL) was added, and the pH was adjusted to ~9-10 by the addition of 1 M aq. NaOH. To the cold reaction mixture was then added $NaBH_4$ (27 mg, 0.711 mmol, 14.0 equiv), and the reaction stirred at 0° C. for 20 min (reaction progress monitored by LCMS). The excess $NaBH_4$ was then destroyed by drop-wise addition of AcOH. The reaction was then basified to pH~9-10 with 1 M aq. NaOH, and the mixture was extracted with $CH_2Cl_2$ (×3). The combined organic layers were dried over $Na_2SO_4$, filtered, and concentrated in vacuo. Purification by preparatory TLC (two elutions with 45:55 EtOAc/hexanes) provided ajmalicine (6.4 mg, 45% yield) as a colorless amorphous solid.

Analytical data for 7: $[\alpha]_D^{25}$: −60.0° (c 0.05, $CHCl_3$); IR (film) 3400, 2923, 1687, 1615, 1438 $cm^{-1}$; $^1$H NMR (500 MHz, $CDCl_3$) δ 7.90 (s, 1H), 7.53 (d, J=1.8 Hz, 1H), 7.46 (dd, J=7.7, 1.1 Hz, 1H), 7.30 (dd, J=8.0, 0.9 Hz, 1H), 7.14 (ddd, J=8.2, 7.0, 1.3 Hz, 1H), 7.08 (ddd, J=8.1, 7.1, 1.1 Hz, 1H), 4.43 (qd, J=6.6, 3.9 Hz, 1H), 3.74 (s, 3H), 3.41 (dd, J=11.3, 2.3 Hz, 1H), 3.20 (dt, J=12.5, 3.1 Hz, 1H), 3.11 (dd, J=11.0, 5.8 Hz, 1H), 3.06-2.97 (m, 1H), 2.98 (dd, J=10.8, 3.0 Hz, 1H), 2.77-2.72 (m, 1H), 2.69 (td, J=11.1, 4.4 Hz, 1H), 2.44 (tdd, J=11.4, 3.6, 1.9 Hz, 1H), 2.26 (t, J=10.9 Hz, 1H), 2.15 (tt, J=11.2, 3.4 Hz, 1H), 1.31 (q, J=11.6 Hz, 1H), 1.19 (d, J=6.6 Hz, 3H). $^{13}$C NMR (125 MHz, $CDCl_3$) δ 167.6, 154.8, 136.1, 134.5, 127.4, 121.6, 119.5, 118.2, 111.0, 108.1, 106.8, 73.9, 60.3, 57.1, 53.4, 51.1, 41.2, 33.1, 30.8, 22.0, 15.1. HRMS (ESI): Mass calcd for $C_{21}H_{25}N_2O_3$ $[M+H]^+$=353.1865; found 353.1867.

Example 20

Alstonine Hydrogen Maleate (1×)

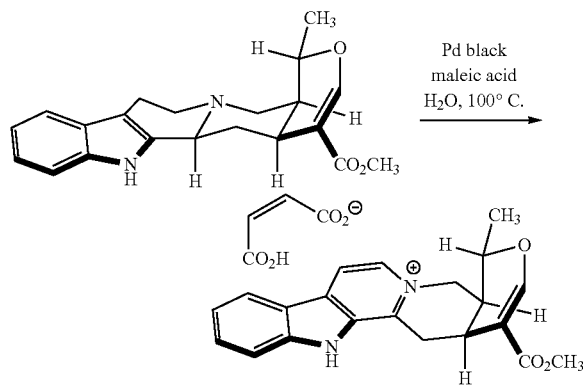

To a solution of tetrahydroalstonine (4.0 mg, 0.011 mmol) in water (0.35 mL, 0.03 M), was added cis-maleic acid (6.6 mg, 0.057 mmol, 5.00 equiv) and palladium black (4.0 mg, 0.037 mmol, 3.30 equiv). The resulting suspension was heated to reflux for 18 h (reaction progress monitored by LCMS), and then the reaction was cooled to ambient temperature. The suspension was taken up in hot methanol and filtered through a pad of Celite. The pad was then rinsed through with additional hot methanol, and the combined filtrate was concentrated in vacuo. Purification by preparatory TLC (15:85 $CH_3OH/CH_2Cl_2$) provided alstonine hydrogen maleate (2.7 mg, 51% yield) as a pale yellow film.

Analytical Data for 1×: $[\alpha]_D^{25}$: 108.0° (c 0.05, $CH_3OH$); $^1$H NMR (500 MHz, Methanol-d4) δ 8.53 (d, J=6.5 Hz, 1H), 8.47 (d, J=6.5 Hz, 1H), 8.39 (dt, J=8.1, 1.1 Hz, 1H), 7.83-7.75 (m, 2H), 7.75 (s, 1H), 7.47 (ddd, J=8.1, 6.8, 1.2 Hz, 1H), 6.25 (s, 1H), 5.04 (dd, J=14.4, 5.9 Hz, 1H), 4.70 (dd, J=14.5, 5.2 Hz, 1H), 4.18 (dd, J=17.7, 6.3 Hz, 1H), 4.03 (dq, J=9.7, 6.2 Hz, 1H), 3.80 (s, 3H), 3.38 (dd, J=17.7, 9.3 Hz, 1H), 3.22 (dtd, J=9.2, 6.3, 1.1 Hz, 1H), 2.57 (dq, J=9.6, 5.8 Hz, 1H), 1.49 (d, J=6.2 Hz, 3H). $^{13}$C NMR (125 MHz, Methanol-d4) δ 170.8, 168.8, 157.2, 145.5, 141.5, 136.8, 135.3, 133.9, 133.5, 133.1, 124.2, 123.2, 121.5, 116.9, 113.9, 109.2, 72.4, 55.7, 52.0, 37.2, 30.0, 27.6, 18.6. HRMS (ESI): Mass calcd for $C_{21}H_{21}N_2O_3^+$ $[M]^+$=349.1547; found 349.1554.

Example 21

Serpentine Methoxide (2×)

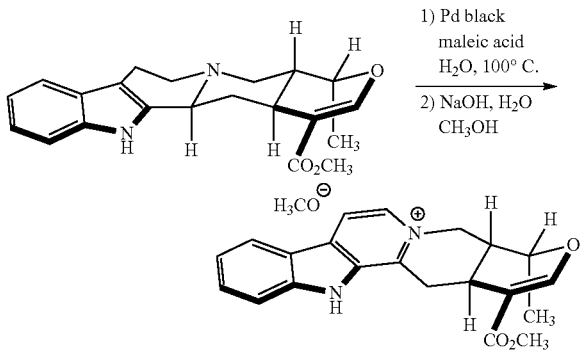

To a solution of ajmalicine (3.5 mg, 9.93 μmol) in water (0.31 mL, 0.03 M), was added cis-maleic acid (5.8 mg, 0.050 mmol, 5.00 equiv) and palladium black (3.5 mg, 0.033 mmol, 3.30 equiv). The resulting suspension was heated to reflux for 20 h, whereupon a second portion of palladium black (2.3 mg, 0.022 mmol, 2.20 equiv) was added. After another 24 h at reflux, reaction was cooled to ambient temperature (reaction progress monitored by LCMS). The suspension was taken up in hot methanol and filtered through a pad of Celite. The pad was then rinsed through with additional hot methanol, and the combined filtrate was concentrated in vacuo. The unpurified mixture was then suspended in 1.0 mL of $CH_3OH$, and 10% aq. NaOH is added until pH of mixture reaches ~10. The mixture was extracted with $CH_2Cl_2$ (×10), the combined organic layers were then passed through a phase separator and concentrated in vacuo. Purification by preparatory TLC (15:85 $CH_3OH/CH_2Cl_2$) provided serpentine methoxide (0.9 mg, 26% yield) as a pale yellow film.

Analytical Data for 2x: $[\alpha]_D^{20}$: 264.4° (c 0.05, CH$_3$OH); $^1$H NMR (500 MHz, methanol-d4) δ 8.52 (d, J=6.6 Hz, 1H), 8.38 (dt, J=8.1, 1.0 Hz, 1H), 8.35 (d, J=6.6 Hz, 1H), 7.83-7.76 (m, 2H), 7.73 (d, J=1.6 Hz, 1H), 7.47 (ddd, J=8.1, 6.1, 2.0 Hz, 1H), 4.91 (dd, J=13.4, 4.3 Hz, 1H), 4.77 (dd, J=6.8, 4.1 Hz, 1H), 4.73 (dd, J=18.4, 5.0 Hz, 1H), 4.65 (t, J=13.0 Hz, 1H), 3.83 (s, 3H), 3.21 (dd, J=18.3, 11.5 Hz, 1H), 3.14-3.07 (m, 1H), 2.73 (tt, J=11.9, 4.1 Hz, 1H), 1.36 (d, J=6.7 Hz, 3H). $^{13}$C NMR (125 MHz, Methanol-d4) δ 168.4, 156.3, 145.5, 141.3, 136.0, 134.2, 132.9, 132.7, 124.1, 123.2, 121.4, 116.9, 114.0, 107.2, 73.0, 57.6, 51.8, 38.5, 30.8, 25.9, 14.2. HRMS (ESI): Mass calcd for $C_{21}H_{21}N_2O_3^+$ [M]$^+$=349.1547; found 349.1556.

Example 22

Determination of Absolute Stereochemistry of 15

The absolute stereochemistry of 15 was determined by X-ray diffraction. Recrystallized from CH$_2$Cl$_2$/hexanes.

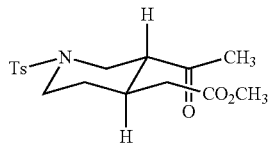 [SMILES: COC(=O)CC1CCN(S(=O)(=O)c2ccc(C)cc2)CC1C(C)=O]

Figure 5:
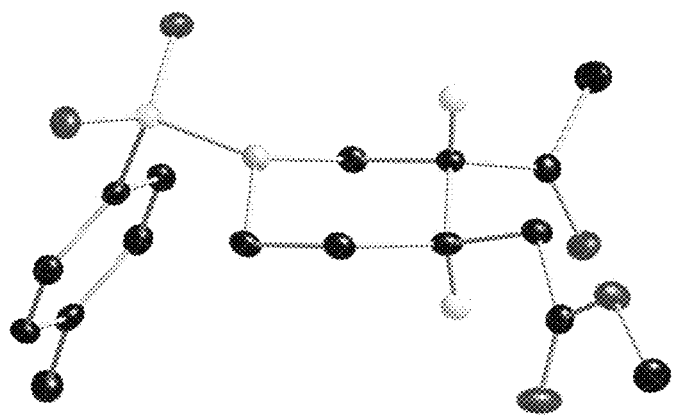

X-ray crystal structure of methyl 2-((3R,4R)-3-acetyl-1-tosylpiperidin-4-yl)acetate (15): X-ray diffraction was performed at 100 K and raw frame data were processed using SAINT. Molecular structures was solved using direct methods and refined on F2 by full-matrix least-square techniques. The GOF=1.052 for 220 variables refined to R1=0.0202 for 2835 reflections with I>2α(I). A multi-scan absorption correction was performed and the Flack parameter was 0.053 (4). (See schematic x-ray structure of FIG. 5.) Further information can be found in the CIF file. This crystal structure was deposited in the Cambridge Crystallographic Data Centre and assigned as CCDC 1030168.

Example 23

Confirmation of Olefin Geometry of 19
The olefin geometry of 19 was confirmed by X-ray diffraction. Recrystallized from CH$_2$Cl$_2$/hexanes.

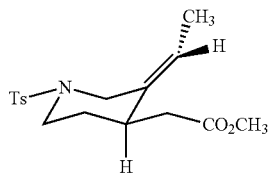

Figure 6:
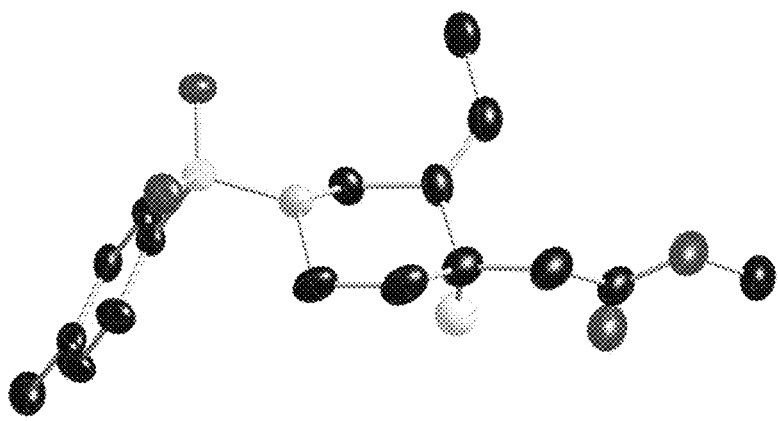

X-ray crystal structure of methyl (Z)-2-(3-ethylidene-1-tosylpiperidin-4-yl)acetate (19): X-ray diffraction was performed at 99.97 K and raw frame data were processed using SAINT. Molecular structures was solved using direct methods and refined on F2 by full-matrix least-square techniques. The GOF=1.123 for 211 variables refined to R1=0.0582 for 2816 reflections with I>2α(I). A multi-scan absorption correction was performed. (See schematic x-ray structure of FIG. 6.) Further information can be found in the CIF file. This crystal structure was deposited in the Cambridge Crystallographic Data Centre and assigned as CCDC 1040072.

Example 24

Various starting materials and resulting compounds are described herein or can be provided with an amino-protecting group. The term "protecting group," as used herein, is well known in the art and include those described in detail in Protecting Groups in Organic Synthesis, T.W. Greene and P.G.M. Wuts, 3rd edition, John Wiley & Sons, 1999, the entirety of which is incorporated herein by reference. Suitable amino-protecting groups include, for instance, methyl carbamate, ethyl carbamate, 9-fluorenylmethyl carbamate (Fmoc), t-butyl carbamate (BOC), benzyl carbamate (Cbz), N-2,5-dimethylpyrrole, p-toluenesulfonamide (Ts) and methanesulfanomide (Ms). Various other protecting groups useful in conjunction with this invention are well-known to those skilled in the art.

We claim:
1. A method of preparing a trans-bicyclic dihydropyran compound, said method comprising:
providing a trans-piperdinyl compound of a formula

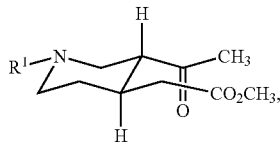

wherein R$^1$ is selected from H and a tosylate protecting group, wherein said trans-piperdinyl compound is provided by reacting a methyl (E)-5-(N-oxobutyl)amninopent-2-enoate with a catalytic amount of (R)-1-naphthalen-1-yl)ethanamine in the presence of an H-bond donor selected from catechol and binol;
reduction of the ketone moiety of said piperdinyl compound to provide a hydroxy ester compound of a formula

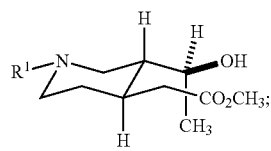

condensation of the hydroxy and ester moieties of said hydroxy ester compound to provide a lactone compound of a formula

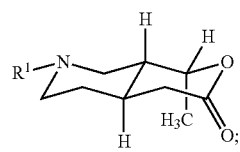

acylation of said lactone compound to provide a formyl lactone of a formula

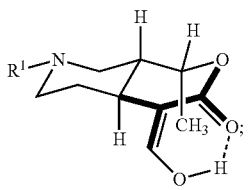

and sequential acetylation of said formyl lactone compound and acid catalyzed elimination of the carbonyl moiety of said lactone to provide a trans-bicyclic dihydropyran compound of a formula

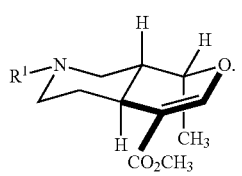

2. The method of claim 1 wherein said condensation is promoted with p-toluenesulfonic acid.

3. The method of claim 1 wherein said acylation is achieved with methyl formate and acyl chloride.

4. The method of claim 3 wherein said acid catalyst is polyphosphoric acid.

5. The method of claim 1 wherein $R^1$ is a tosylate (Ts) protecting group.

* * * * *